United States Patent
St. Onge et al.

(10) Patent No.: US 10,787,661 B2
(45) Date of Patent: Sep. 29, 2020

(54) SCALABLE METHOD FOR ISOLATION AND SEQUENCE-VERIFICATION OF OLIGONUCLEOTIDES FROM COMPLEX LIBRARIES

(71) Applicant: The Board of Trustees of the Leland Stanford Junior University, Palo Alto, CA (US)

(72) Inventors: Robert P. St. Onge, Palo Alto, CA (US); Ulrich Schlecht, Palo Alto, CA (US); Sasha F. Levy, Stony Brook, NY (US); Ronald W. Davis, Palo Alto, CA (US); Joseph Horecka, Fremont, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 751 days.

(21) Appl. No.: 14/928,928

(22) Filed: Oct. 30, 2015

(65) Prior Publication Data
US 2016/0122748 A1    May 5, 2016

Related U.S. Application Data

(60) Provisional application No. 62/072,759, filed on Oct. 30, 2014.

(51) Int. Cl.
C12N 15/10    (2006.01)

(52) U.S. Cl.
CPC ..... C12N 15/1037 (2013.01); C12N 15/1031 (2013.01); C12N 15/1034 (2013.01); C12N 15/1058 (2013.01)

(58) Field of Classification Search
None
See application file for complete search history.

(56) References Cited

U.S. PATENT DOCUMENTS

| | | | |
|---|---|---|---|
| 8,268,564 B2 | 9/2012 | Roth et al. | |
| 2003/0027213 A1* | 2/2003 | Zhu | C07K 16/00 435/7.1 |
| 2010/0216648 A1* | 8/2010 | Staehler | C12Q 1/6869 506/6 |
| 2011/0124075 A1* | 5/2011 | Amerik | C12N 15/01 435/171 |
| 2011/0319290 A1 | 12/2011 | Raymond et al. | |
| 2012/0283110 A1 | 11/2012 | Shendure et al. | |

OTHER PUBLICATIONS

Yan et al. (Nature methods 5.8 (2008): 719) (Year: 2008).*
Chen et al. (BMC genomics 13.1 (2012): 161.) (Year: 2012).*
Silva et al. (Nature genetics 37.11 (2005): 1281.). (Year: 2005).*
Yan 2008 supp (Year: 2008).*
Kuijpers et al. ( FEMS yeast research 13.8 (2013): 769-781; published online Oct. 7, 2013). (Year: 2013).*
Mecham et al. ( Physiological Genomics 18.3 (2004): 308-315.). (Year: 2004).*
Matzas et al. ( Nature biotechnology 28.12 (2010): 1291). (Year: 2010).*
Labunskyy et al. (Genetics 4.7 (2014): 1183-1191; published online Apr. 28, 2014) (Year: 2014).*
Suzuki et al. (Nature Methods 8.2 (2011): 159) (Year: 2011).*
Douglas et al.( G3: Genes, Genomes, Genetics 2.10 (2012): 1279-1289) (Year: 2012).*
Kuijpers et al. (Microbial cell factories 12.1 (2013): 47.; published online May 2013) (Year: 2013).*
Hull et al. (2013) Sequencing and de novo assembly of the western tarnished plant bug (Lygus hesperus) transcriptome. PLoS One 8(1):e55105.
Schwartz et al. (2012) Accurate gene synthesis with tag-directed retrieval of sequence-verified DNA molecules. Nat Methods 9(9):913-915.
Yu et al. (2011) Development of expression-ready constructs for generation of proteomic libraries. Methods Mol Biol 723:257-272.
MATZASat et al. (2010) High-fidelity gene synthesis by retrieval of sequence-verified Dna identified using high-throughput pyrosequencing. Nat Biotechnol 28(12):1291-1294.
Blommel et al. (2009) Flexi vector cloning. Methods Mol Biol 498:55-73.
Bechtel et al. (2007) The full-ORF clone resource of the German cDNA Consortium. BMC Genomics 8:399.
Thao et al. (2004) Results from high-throughput DNA cloning of Arabidopsis thaliana target genes using site-specific recombination. J Struct Funct Genomics 5(4):267-276.
Mecham et al. (2004) Increased measurement accuracy for sequence-verified microarray probes. Physiol Genomics 18(3):308-315.
Taylor et al. (2001) Sequence verification as quality-control step for production of cDNA microarrays. Biotechniques 31(1):62-65.
Peikon et al. (2014) In vivo generation of DNA sequence diversity for cellular barcoding. Nucleic Acids Res 42(16):e127.
Sauer et al. (1987) Functional expression of the cre-lox site-specific recombination system in the yeast Saccharomyces cerevisiae. Mol Cell Biol. 7(6):2087-2096.
Lefrancois et al. (2009) Efficient yeast ChIP-Seq using multiplex short-read DNA sequencing. BMC Genomics 10:37.
Eroshenko et al. (2012) Gene Assembly from Chip-Synthesized Oligonucleotides. Curr Protoc Chem Biol 2012. pii: ch110190.
Wong et al. (2013) Multiplex Illumina sequencing using DNA barcoding. Curr Protoc Mol Biol. Chapter 7:Unit 7.11.

* cited by examiner

*Primary Examiner* — Tracy Vivlemore
*Assistant Examiner* — Sahana S Kaup
(74) *Attorney, Agent, or Firm* — Mintz, Levin, Cohn, Ferris, Glovsky and Popeo, P.C.

(57) ABSTRACT

A novel method for preparing sequence-verified oligonucleotides is disclosed. In particular, the invention relates to a simple, affordable, and scalable method that combines high-throughput mating of yeast clones, a unique selectable system for combining DNA sequences in yeast, and next-generation sequencing. This method allows sequence-verified oligonucleotides to be readily isolated from complex libraries.

42 Claims, 14 Drawing Sheets

Specification includes a Sequence Listing.

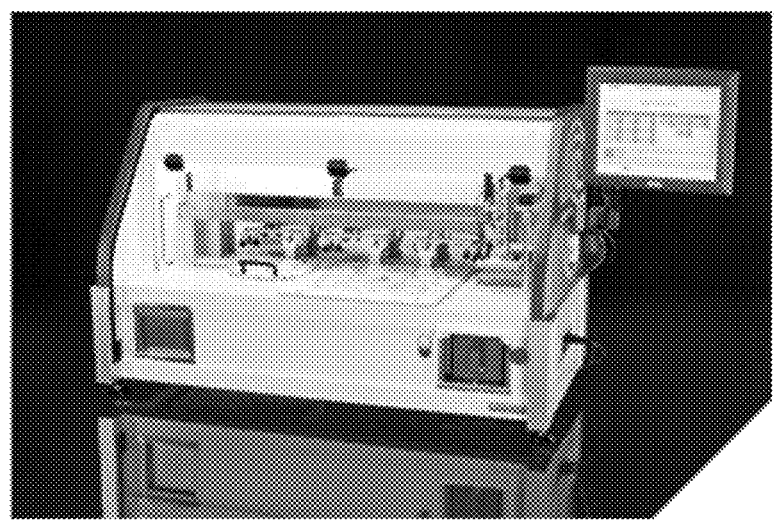
The ROTOR: high density replica plating and mating of ordered arrays
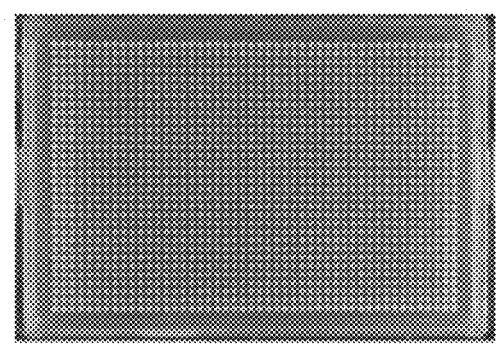
1536 yeast colonies
FIG. 2B

BARCODE

ATTGCAATCATATTCTAGCTTATTGC...oligo X
ATGAGAAACTGTTCAATCTTCAGTA...oligo Y
CCATGAAGGCTATTGTTCATTATTTT...oligo Z
ATTGCAATCATATTCTAGCTTATTGC...oligo X
...many more sequence reads...

FIG. 3C

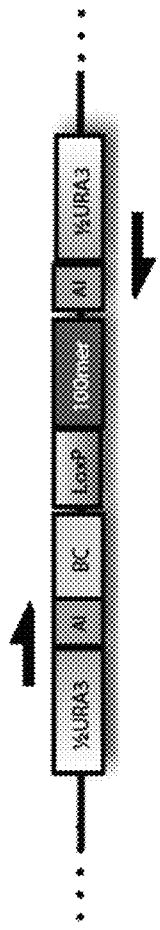
FIG. 3D

- Synthesized 7051 DNA probes (145mers) targeting >300 bacteria (CustomArray)
- Amplified and transformed this library into our recipient strain
- Processed ~35k transformants & identified ~3500 'perfect', sequence-verified probes
- Picked clones for 3322 probes (see image below)
- Individual probes can be accessed at any time
- *IDT cost = $385,352, our reagent cost = ~$3,000

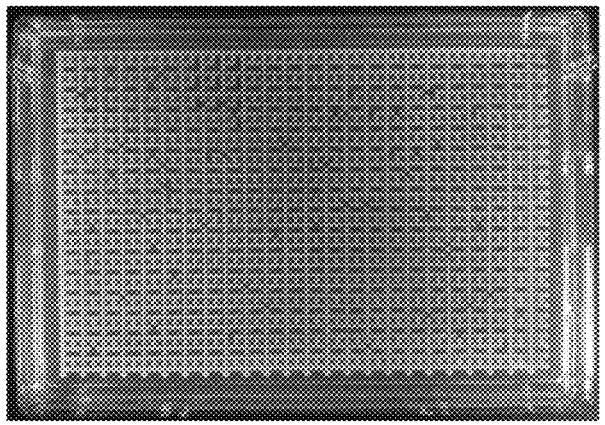

Agar plate containing 3322 clones, each harboring a unique sequence-verified molecular probe.

FIG. 7

SEQUENCE LISTING

<160> NUMBER OF SEQ ID NOS: 15

<210> SEQ ID NO 1
<211> LENGTH: 20
<212> TYPE: DNA
<213> ORGANISM: Artificial Sequence
<220> FEATURE:
<223> OTHER INFORMATION: Ras mutagenesis 3' flanking sequence
<220> FEATURE:
<221> NAME/KEY: source
<222> LOCATION: (1)..(20)
<223> OTHER INFORMATION: sequence is synthesized

<400> SEQUENCE: 1
cgagtgactc cttccgatct                                              20

<210> SEQ ID NO 2
<211> LENGTH: 60
<212> TYPE: DNA
<213> ORGANISM: Artificial Sequence

```
<220> FEATURE:
<223> OTHER INFORMATION: ras fragment forward primer
<220> FEATURE:
<221> NAME/KEY: source
<222> LOCATION: (1)..(60)
<223> OTHER INFORMATION: sequence is synthesized

<400> SEQUENCE: 2
gactaaagga ggcttttgtc gacggatccg atatcggtac gacctgcagt gagtcgtacg      60

<210> SEQ ID NO 3
<211> LENGTH: 60
<212> TYPE: DNA
<213> ORGANISM: Artificial Sequence
<220> FEATURE:
<223> OTHER INFORMATION: ras fragment reverse primer
<220> FEATURE:
<221> NAME/KEY: source
<222> LOCATION: (1)..(60)
<223> OTHER INFORMATION: sequence is synthesized

<400> SEQUENCE: 3
ttatacgaag ttatgttgca acacacttcc tgcttaggca agatcggaag gagtcactcg      60

<210> SEQ ID NO 4
<211> LENGTH: 21
<212> TYPE: DNA
<213> ORGANISM: Artificial Sequence
<220> FEATURE:
<223> OTHER INFORMATION: M13 forward primer
<220> FEATURE:
<221> NAME/KEY: source
<222> LOCATION: (1)..(21)
<223> OTHER INFORMATION: sequence is synthesized

<400> SEQUENCE: 4
gttgtaaaac gacggccagt g                                                21

<210> SEQ ID NO 5
<211> LENGTH: 23
<212> TYPE: DNA
<213> ORGANISM: Artificial Sequence
<220> FEATURE:
<223> OTHER INFORMATION: M13 reverse primer
<220> FEATURE:
<221> NAME/KEY: source
<222> LOCATION: (1)..(23)
<223> OTHER INFORMATION: sequence is synthesized

<400> SEQUENCE: 5
tcacacagga aacagctatg acc                                              23

<210> SEQ ID NO 6
<211> LENGTH: 83
<212> TYPE: DNA
<213> ORGANISM: Artificial Sequence
<220> FEATURE:
<223> OTHER INFORMATION: DBC-UP-1 primer
<220> FEATURE:
<221> NAME/KEY: source
<222> LOCATION: (1)..(83)
<223> OTHER INFORMATION: sequence is synthesized

<400> SEQUENCE: 6
aatgatacgg cgaccaccga gatctacact ctttccctac acgacgctct tccgatcttg      60
ctaaacggat ccgatatcgg tac                                              83

<210> SEQ ID NO 7
```

```
<211> LENGTH: 87
<212> TYPE: DNA
<213> ORGANISM: Artificial Sequence
<220> FEATURE:
<223> OTHER INFORMATION: DBC-DN-5 primer
<220> FEATURE:
<221> NAME/KEY: source
<222> LOCATION: (1)..(87)
<223> OTHER INFORMATION: sequence is synthesized

<400> SEQUENCE: 7
caagcagaag acggcatacg agatcggtct cggcattcct gctgaaccgc tcttccgatc    60
tatgatctta gatctgatat cggtacc                                        87

<210> SEQ ID NO 8
<211> LENGTH: 20
<212> TYPE: DNA
<213> ORGANISM: Artificial Sequence
<220> FEATURE:
<223> OTHER INFORMATION: ras forward PCR primer
<220> FEATURE:
<221> NAME/KEY: source
<222> LOCATION: (1)..(20)
<223> OTHER INFORMATION: sequence is synthesized

<400> SEQUENCE: 8
gacctgcagt gagtcgtacg                                                20

<210> SEQ ID NO 9
<211> LENGTH: 20
<212> TYPE: DNA
<213> ORGANISM: Artificial Sequence
<220> FEATURE:
<223> OTHER INFORMATION: ras reverse PCR primer
<220> FEATURE:
<221> NAME/KEY: source
<222> LOCATION: (1)..(20)
<223> OTHER INFORMATION: sequence is synthesized

<400> SEQUENCE: 9
agatcggaag gagtcactcg                                                20

<210> SEQ ID NO 10
<211> LENGTH: 26
<212> TYPE: DNA
<213> ORGANISM: Artificial Sequence
<220> FEATURE:
<223> OTHER INFORMATION: oligo X barcode
<220> FEATURE:
<221> NAME/KEY: source
<222> LOCATION: (1)..(26)
<223> OTHER INFORMATION: sequence is synthesized

<400> SEQUENCE: 10
attgcaatca tattctagct tattgc                                         26

<210> SEQ ID NO 11
<211> LENGTH: 26
<212> TYPE: DNA
<213> ORGANISM: Artificial Sequence
<220> FEATURE:
<223> OTHER INFORMATION: oligo Y barcode
<220> FEATURE:
<221> NAME/KEY: source
<222> LOCATION: (1)..(26)
<223> OTHER INFORMATION: sequence is synthesized

<400> SEQUENCE: 11
atgagaaaac tgttcaatct tcagta                                         26
```

```
<210> SEQ ID NO 12
<211> LENGTH: 26
<212> TYPE: DNA
<213> ORGANISM: Artificial Sequence
<220> FEATURE:
<223> OTHER INFORMATION: oligo Z barcode
<220> FEATURE:
<221> NAME/KEY: source
<222> LOCATION: (1)..(26)
<223> OTHER INFORMATION: sequence is synthesized

<400> SEQUENCE: 12
ccatgaaggc tattgttcat tatttt                                          26

<210> SEQ ID NO 13
<211> LENGTH: 40
<212> TYPE: DNA
<213> ORGANISM: Artificial Sequence
<220> FEATURE:
<223> OTHER INFORMATION: clone A
<220> FEATURE:
<221> NAME/KEY: source
<222> LOCATION: (1)..(40)
<223> OTHER INFORMATION: sequence is synthesized

<400> SEQUENCE: 13
gtctgtcagt ggagagggtg aaggtgatgc aacatacgga                           40

<210> SEQ ID NO 14
<211> LENGTH: 40
<212> TYPE: DNA
<213> ORGANISM: Artificial Sequence
<220> FEATURE:
<223> OTHER INFORMATION: clone C
<220> FEATURE:
<221> NAME/KEY: source
<222> LOCATION: (1)..(40)
<223> OTHER INFORMATION: sequence is synthesized

<400> SEQUENCE: 14
ttctgtcagt ggagagggtg aaggtgatgc aacatacgga                           40

<210> SEQ ID NO 15
<211> LENGTH: 26
<212> TYPE: DNA
<213> ORGANISM: Artificial Sequence
<220> FEATURE:
<223> OTHER INFORMATION: barcode sequence
<220> FEATURE:
<221> NAME/KEY: source
<222> LOCATION: (1)..(26)
<223> OTHER INFORMATION: sequence is synthesized

<400> SEQUENCE: 15
tgcctaagca ggaagtgtgt tgcaac                                          26
```

SCALABLE METHOD FOR ISOLATION AND SEQUENCE-VERIFICATION OF OLIGONUCLEOTIDES FROM COMPLEX LIBRARIES

CROSS REFERENCE TO RELATED APPLICATIONS

This application claims priority to U.S. Provisional Application No. 62/072,759, filed Oct. 30, 2014, which is hereby incorporated by reference in its entirety and for all purposes.

STATEMENT REGARDING FEDERALLY SPONSORED RESEARCH OR DEVELOPMENT

This invention was made with Government support under contracts GM110706, HG000205, and HG003328 awarded by the National Institutes of Health. The Government has certain rights in the invention.

TECHNICAL FIELD

The present invention pertains generally to oligonucleotide library preparation and sequence verification. In particular, the invention relates to methods for isolating sequence-verified oligonucleotides from complex mixtures.

BACKGROUND

Array-based oligonucleotide synthesis is a powerful platform for a variety of biological applications including targeted DNA sequencing, metagenomic profiling, functional genomic screening, antibody engineering, genome editing, and gene synthesis. The principle benefit of array-synthesized oligonucleotides is cost, which is typically 2-4 orders of magnitude lower than column-synthesized oligonucleotides. However, there are several drawbacks that limit their utility. First, oligonucleotides are delivered as complex pools, and retrieving sub-sets of individual oligonucleotides from complex libraries is imperfect and requires set-specific common priming sites to be included in their design. In addition, array-based DNA synthesis suffers from relatively high error-rates and low yields.

The aforementioned inadequacies of current DNA synthesis platforms limit the application of synthetic DNA in biology and medicine. Thus, there remains a need for the development of improved methods for preparing and isolating oligonucleotides that reduce errors and provide sequence verification.

SUMMARY

The present invention relates to methods for isolating sequence-verified oligonucleotides from complex mixtures. The methods combine high-throughput production of clones comprising an oligonucleotide library, barcoding of clones to allow ready identification of clones comprising desired oligonucleotides, and next-generation sequencing for sequence verification. In particular, the methods utilize recipient host strains for efficient incorporation of oligonucleotides by transformation and barcoder strains for tagging oligonucleotides to allow ready identification of clones containing desired oligonucleotides from pooled mixtures.

In one aspect, the invention includes a method for isolating a sequence-verified oligonucleotide from a composition comprising a mixture of oligonucleotides (e.g., oligonucleotide library). The method comprises: a) providing the composition comprising the mixture of oligonucleotides, wherein each oligonucleotide comprises an unknown sequence and common priming sites for amplification; b) amplifying one or more oligonucleotides; c) transforming a plurality of host cells with the amplified oligonucleotides; d) plating the plurality of transformed host cells in an ordered array on media suitable for growth of the host cells; e) culturing the plurality of transformed host cells under conditions whereby each host cell produces a colony of clones in the ordered array; f) introducing an oligonucleotide from a colony in the ordered array into a barcoder cell, wherein the barcoder cell comprises a nucleic acid comprising a recombination target site for a site-specific recombinase and a barcode sequence that identifies the colony in the ordered array to which the oligonucleotide corresponds; g) translocating the oligonucleotide to a position adjacent to the barcode sequence of the barcoder cell using a site-specific recombinase system, wherein site-specific recombination with the recombination target site of the barcoder cell generates a nucleic acid comprising a barcode-oligonucleotide fusion sequence; h) sequencing the barcode-oligonucleotide fusion sequence to identify a colony in the ordered array comprising a sequence-verified oligonucleotide; i) picking a clone comprising the sequence-verified oligonucleotide from the colony in the ordered array identified by the barcode; and j) isolating the sequence-verified oligonucleotide from the clone. In certain embodiments, the mixture of oligonucleotides comprises a probe library or a primer library. Plating of cells in an ordered array as well as clone picking from an ordered array of cells can be performed with an automated robotic device or manually. The method may further comprise amplifying a sequence-verified oligonucleotide before use in downstream applications. In one embodiment, the method further comprises removing contaminating oligonucleotides that have incorrect sequences from an oligonucleotide library.

In certain embodiments, oligonucleotides are integrated into the genome of a host cell at a target locus. For example, a targeting sequence may be added to each oligonucleotide, wherein the targeting sequence is sufficiently homologous to a genomic target locus of the host cell such that the oligonucleotide integrates into the genome at the target locus in the transformed host cell by homologous recombination. In one embodiment, the oligonucleotides are amplified with a primer comprising an integration targeting sequence that is sufficiently homologous to a genomic target locus of the host cell, such that amplicons of the oligonucleotides integrate into the genome at the target locus in the transformed host cell by homologous recombination. In order to facilitate genomic integration at the target locus, a host cell may also be transformed with a recombinant polynucleotide encoding a restriction enzyme operably linked to a promotor, wherein the restriction enzyme creates a double strand break at the genomic target locus that assists homologous recombination. In addition, a selectable marker may be used that selects for clones that have undergone successful integration of an oligonucleotide at the genomic target locus.

In other embodiments, oligonucleotides are integrated into a plasmid of a host cell at a particular target locus. For example, a plasmid targeting sequence may be added to each oligonucleotide, wherein the targeting sequence is sufficiently homologous to a target locus on a plasmid in the host cell, such that the oligonucleotide integrates into the plasmid at the target locus in the transformed host cell. In one embodiment, the oligonucleotides are amplified with a primer comprising a targeting sequence that is sufficiently homologous to a target locus on a plasmid in the host cell, such that the oligonucleotide amplicons integrate into the plasmid at the target locus in the transformed host cell. In order to facilitate integration at the plasmid target locus, a host cell may also be transformed with a recombinant polynucleotide encoding a restriction enzyme operably linked to a promotor, wherein the restriction enzyme creates a double strand break at the plasmid target locus that assists homologous recombination. In addition, a selectable marker may be used that selects for clones that have undergone successful integration of an oligonucleotide at the plasmid target locus.

In another embodiment, the oligonucleotides are provided in vectors for transformation of the host cells. In one embodiment, the unknown sequence of each oligonucleotide is flanked by a common 5' restriction site and a common 3' restriction site. The method further comprises performing a restriction digest that selectively cleaves each oligonucleotide at the common 5' restriction site and the common 3' restriction site to produce restriction fragments, which can be cloned into vectors (e.g., plasmids or viral vectors). The plurality of host cells is then transformed with the vectors comprising the oligonucleotides.

In certain embodiments, the host cells are prokaryotic cells or eukaryotic cells. In one embodiment, the host cells are yeast cells. In another embodiment, the host cells are bacteria.

Translocation of an oligonucleotide adjacent to a barcode sequence can be performed with any suitable site-specific recombinase system. Exemplary site-specific recombinase systems include Cre-loxP, Flp-FRT, PhiC31-att, and Dre-rox site-specific recombinase systems. In addition, a selectable marker may be used that selects for clones that have undergone successful site-specific recombination.

A recombination target site for a site-specific recombinase can be linked to an oligonucleotide in a number of ways. For example, an oligonucleotide can be amplified with a primer comprising a recombination target site capable of undergoing recombination with the recombination target site of the barcoder cell. Alternatively, an oligonucleotide can be integrated into the genome or a plasmid in a host cell at a locus adjacent to a recombination target site capable of undergoing recombination with the recombination target site of the barcoder cell to produce a barcode-oligonucleotide fusion sequence.

Amplification of oligonucleotides may be performed before transformation of cells with oligonucleotides or after isolation of sequence verified oligonucleotides from cells. Any method for amplifying oligonucleotides may be used, including, but not limited to polymerase chain reaction (PCR), nucleic acid sequence-based amplification (NASBA), transcription mediated amplification (TMA), strand displacement amplification (SDA), and ligase chain reaction (LCR). In one embodiment, the oligonucleotides comprise common 5' and 3' priming sites to allow amplification of the oligonucleotides in parallel with a set of universal primers. In another embodiment, a set of selective primers is used to selectively amplify a subset of the oligonucleotides from a mixture.

Sequence-verified oligonucleotides can be used, for example, as probes for hybridization-based detection, primers for amplification of nucleic acids or sequencing (e.g., primer libraries for gene expression detection or quantification), or as templates for making small interfering RNAs (siRNAs) or guide RNAs. Additionally, sequence-verified oligonucleotides can be used in various applications, including, but not limited to, CRISPR interference (CRISPRi), SNP genotyping, metagenomics, protein and antibody engineering, allele replacement, gene synthesis, pathway synthesis (e.g., biofuels, new drugs), or genome synthesis.

In another embodiment, the invention includes a method of creating a library (e.g., a probe library or a primer library) of sequence-verified oligonucleotides by collecting clones comprising sequence-verified oligonucleotides produced by the methods described herein.

In another embodiment, the invention includes a method for in vitro gene synthesis, the method comprising: a) isolating a set of sequence-verified oligonucleotides as described herein, wherein the oligonucleotides collectively comprise the sequence of the gene; and b) performing gene assembly with the set of sequence-verified oligonucleotides. Gene assembly may be performed, for example, using ligase chain reaction (LCR) or assembly PCR.

In certain embodiments, yeast is used for isolating sequence-verified oligonucleotides from a composition comprising a mixture of oligonucleotides. In one embodiment, the method comprises: a) providing the composition comprising the mixture of oligonucleotides, wherein each oligonucleotide comprises an unknown sequence and common priming sites for amplification; b) amplifying one or more oligonucleotides; c) transforming a plurality of haploid recipient yeast host cells with the amplified oligonucleotides; d) plating the plurality of transformed recipient yeast host cells in an ordered array on media suitable for growth of the recipient yeast host cells; e) culturing the plurality of transformed recipient yeast host cells under conditions whereby each recipient yeast host cell produces a colony of clones in the ordered array; f) providing a plurality of haploid barcoder yeast cells capable of mating with the recipient yeast host cells, wherein each barcoder yeast cell comprises a nucleic acid comprising a recombination target site for a site-specific recombinase and a barcode sequence that identifies the colony in the ordered array to which the oligonucleotide corresponds; g) mating the plurality of haploid recipient yeast host cells with the plurality of haploid barcoder yeast cells to produce diploid yeast cells; h) translocating the oligonucleotide to a position adjacent to the barcode sequence in each diploid yeast cell using a site-specific recombinase system, wherein site-specific recombination with the recombination target site of the barcoder cell generates a nucleic acid comprising a barcode-oligonucleotide fusion sequence; i) combining diploid yeast cells comprising barcode-oligonucleotide fusion sequences; j) isolating nucleic acids from the diploid cells; k) sequencing one or more barcode-oligonucleotide fusion sequences to identify colonies in the ordered array comprising sequence-verified oligonucleotides; l) picking one or more clones comprising the sequence-verified oligonucleotides from the colonies in the ordered array identified by their barcodes; and m) isolating one or more sequence-verified oligonucleotides from the clones. In one embodiment, recipient yeast host cells of strain MATα are mated with barcoder yeast cells of strain MATa. In another embodiment, recipient yeast host cells of strain MATa are mated with barcoder yeast cells of strain MATα.

In another aspect, the invention includes a method for isolating a sequence-verified cDNA from a composition comprising a mixture of cDNAs, the method comprising: a) providing the composition comprising the mixture of cDNAs, wherein each cDNA comprises an unknown sequence and common priming sites for amplification; b) amplifying one or more cDNAs; c) transforming a plurality of host cells with the amplified cDNAs; d) plating the plurality of transformed host cells in an ordered array on media suitable for growth of the host cells; e) culturing the plurality of transformed host cells under conditions whereby each host cell produces a colony of clones in the ordered array; f) introducing a cDNA from a colony into a barcoder cell, wherein the barcoder cell comprises a nucleic acid comprising a recombination target site for a site-specific recombinase and a barcode sequence that identifies the colony in the ordered array to which the cDNA corresponds; g) translocating the cDNA to a position adjacent to the barcode sequence of the barcoder cell using a site-specific recombinase system, wherein site-specific recombination with the recombination target site of the barcoder cell generates a nucleic acid comprising a barcode-cDNA fusion sequence; h) sequencing the barcode-cDNA fusion sequence to identify a colony comprising a sequence-verified cDNA; i) picking a clone comprising the sequence-verified cDNA from the colony in the ordered array identified by the barcode; and j) isolating the sequence-verified cDNA from the clone.

These and other embodiments of the subject invention will readily occur to those of skill in the art in view of the disclosure herein.

BRIEF DESCRIPTION OF THE FIGURES

FIGS. 2A and 2B show a system for barcoding exogenous DNA in transformed yeast. FIG. 2A shows loxP-mediated recombination in a diploid yeast strain produced from mating of a haploid MATa yeast strain transfected with an oligonucleotide (100mer) from the library and a haploid barcoded MATα yeast strain. In the MATa yeast strain, the oligonucleotide sequence is integrated into the genome where it is positioned between a loxP recombination site and an artificial intron (AI). The MATa genomic construct also contains a portion of a URA3 gene. The barcoded MATα yeast strain also contains a loxP recombination site and the remaining portion of the URA3 gene. LoxP-mediated recombination in the diploid strain results in translocation of the oligonucleotide sequence adjacent to the barcode (BC) sequence and formation of a functional URA3 gene, which is used as a selectable marker. FIG. 2B shows high density replica plating of ordered arrays of yeast colonies using a Singer ROTOR robot.

FIGS. 3A-3E shows steps of the protocol for isolation of sequence-verified oligonucleotides from a pooled mixture of oligonucleotides. FIG. 3A shows steps 1-4, including PCR amplification of oligonucleotides, transformation of a MATa haploid recipient yeast strain with oligonucleotide DNA, integration of oligonucleotide DNA into the yeast genome, and plating transformants in an ordered array. FIG. 3B shows steps 5 and 6, including mating of a transformed MATa strain with a haploid MATα barcoder strain to produce a diploid yeast strain, inducing Cre-LoxP recombination in order to translocate the oligonucleotide sequence to a position adjacent to the barcode sequence in the diploid genome, and selecting recombinants. FIG. 3C shows examples of translocated genomic constructs comprising a barcode sequence (SEQ ID NOS:10-12) connected to an oligonucleotide sequence. FIG. 3D shows steps 7-12, including extraction of DNA from pooled diploid yeast clones, PCR amplification of barcode-oligonucleotide fusion sequences, and sequencing of amplicons. FIG. 3E shows steps 13 and 15, including picking a MATa clone transfected with a sequence-verified oligonucleotide from an ordered array and PCR amplification of the oligonucleotide for use in synthetic biology applications.

FIG. 7 shows the Second Pilot Experiment (DNA Probe Library). 7051 DNA probes (145mers) were synthesized of which about 3500 probes were identified as having a correct sequence. 3322 clones, each harboring a unique sequence-verified molecular probe, were arrayed on an agar plate and can be accessed when needed for various applications.

FIG. 8A shows the purity of the original CustomArray oligonucleotide pool. FIG. 8B shows the purity of the oligonucleotide pool after processing in yeast by our method (see Example 4). After processing, 98% of the DNA in the library had the correct sequence, and individual probes were of similar abundance (x-axis).

DETAILED DESCRIPTION OF THE INVENTION

Figure 1:
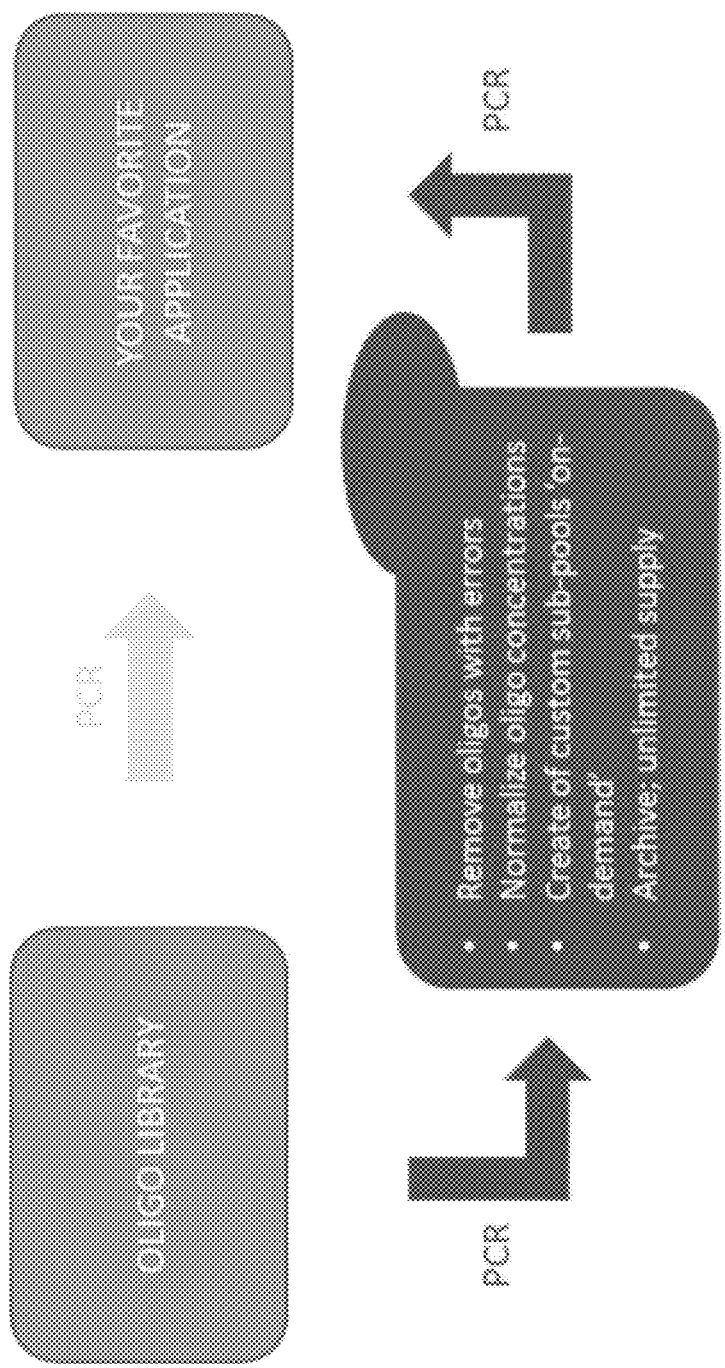
FIG. 1 shows a schematic overview of the method for isolation of sequence-verified oligonucleotides from complex libraries.
Figure 2A:
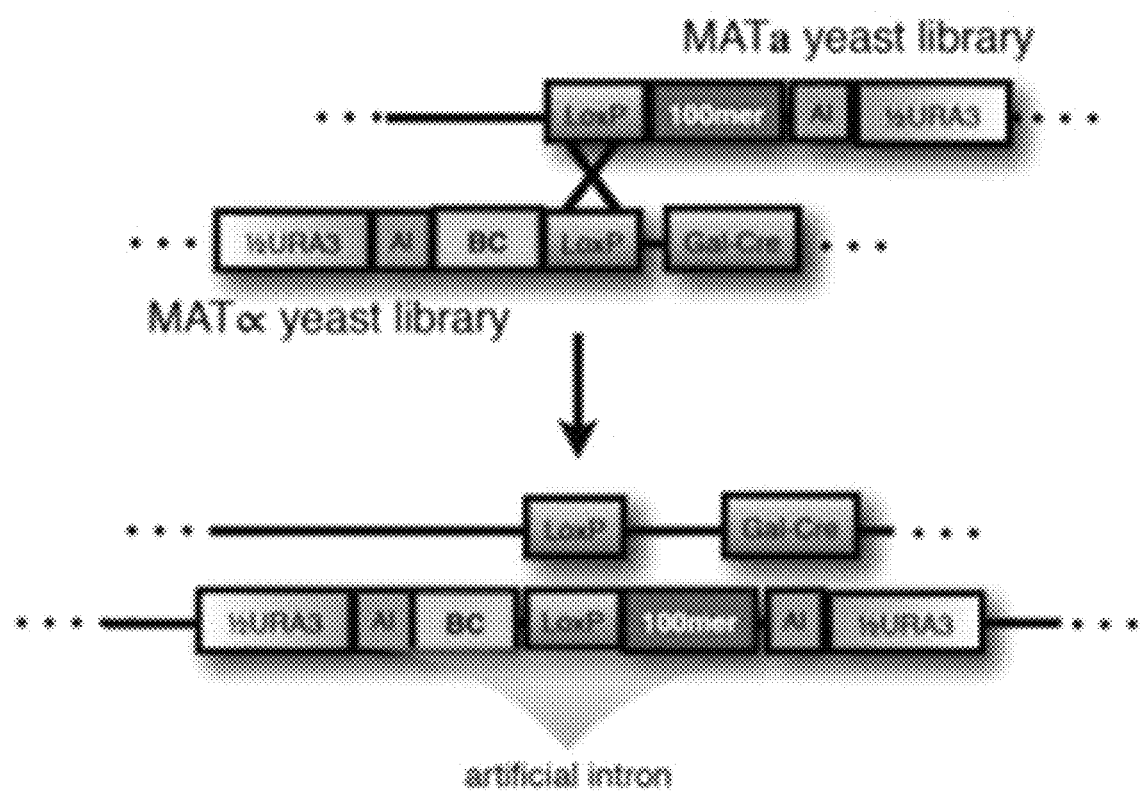

The practice of the present invention will employ, unless otherwise indicated, conventional methods of chemistry, biochemistry, molecular biology and recombinant DNA techniques, within the skill of the art. Such techniques are explained fully in the literature. See, e.g., *Oligonucleotide Synthesis: Methods and Applications* (Methods in Molecular Biology, P. Herdewijn ed., Humana Press, 2005); *Protocols for Oligonucleotides and Analogs: Synthesis and Properties* (Methods in Molecular Biology, S. Agrawal ed., Humana Press, 1993); *Gene Synthesis: Methods and Protocols* (Methods in Molecular Biology, Vol. 852, J. Peccoud ed., Humana Press, 2012); A. L. Lehninger, *Biochemistry* (Worth Publishers, Inc., current addition); Sambrook, et al., *Molecular Cloning: A Laboratory Manual* ($3^{rd}$ Edition, 2001); *Methods In Enzymology* (S. Colowick and N. Kaplan eds., Academic Press, Inc.).

All publications, patents and patent applications cited herein, whether supra or infra, are hereby incorporated by reference in their entireties.

1. DEFINITIONS

In describing the present invention, the following terms will be employed, and are intended to be defined as indicated below.

It must be noted that, as used in this specification and the appended claims, the singular forms "a", "an" and "the" include plural referents unless the content clearly dictates otherwise. Thus, for example, reference to "an oligonucleotide" includes a mixture of two or more such oligonucleotides, and the like.

The terms "oligonucleotide," "polynucleotide," "nucleic acid" and "nucleic acid molecule" are used herein to include a polymeric form of nucleotides of any length, either ribonucleotides or deoxyribonucleotides. This term refers only to the primary structure of the molecule. Thus, the term includes triple-, double- and single-stranded DNA, as well as triple-, double- and single-stranded RNA. It also includes modifications, such as by methylation and/or by capping, and unmodified forms of a polynucleotide. There is no intended distinction in length between the terms "oligonucleotide," "polynucleotide," "nucleic acid" and "nucleic acid molecule," and these terms will be used interchangeably.

The term "barcode" refers to a nucleic acid sequence that is used to identify a single cell or a subpopulation of cells.

The term "barcoder cell" refers to a cell comprising a nucleic acid comprising a barcode sequence.

"Recombinant" as used herein to describe a nucleic acid molecule means a polynucleotide of genomic, cDNA, viral, semisynthetic, or synthetic origin which, by virtue of its origin or manipulation is not associated with all or a portion of the polynucleotide with which it is associated in nature. The term "recombinant" as used with respect to a protein or polypeptide means a polypeptide produced by expression of a recombinant polynucleotide. In general, the gene of interest is cloned and then expressed in transformed organisms, as described further below. The host organism expresses the foreign gene to produce the protein under expression conditions.

The term "primer" or "oligonucleotide primer" as used herein, refers to an oligonucleotide that hybridizes to the template strand of a nucleic acid and initiates synthesis of a nucleic acid strand complementary to the template strand when placed under conditions in which synthesis of a primer extension product is induced, i.e., in the presence of nucleotides and a polymerization-inducing agent such as a DNA or RNA polymerase and at suitable temperature, pH, metal concentration, and salt concentration. The primer is preferably single-stranded for maximum efficiency in amplification, but may alternatively be double-stranded. If double-stranded, the primer can first be treated to separate its strands before being used to prepare extension products. This denaturation step is typically effected by heat, but may alternatively be carried out using alkali, followed by neutralization. Thus, a "primer" is complementary to a template, and complexes by hydrogen bonding or hybridization with the template to give a primer/template complex for initiation of synthesis by a polymerase, which is extended by the addition of covalently bonded bases linked at its 3' end complementary to the template in the process of DNA or RNA synthesis. Typically, nucleic acids are amplified using at least one set of oligonucleotide primers comprising at least one forward primer and at least one reverse primer capable of hybridizing to regions of a nucleic acid flanking the portion of the nucleic acid to be amplified.

The term "amplicon" refers to the amplified nucleic acid product of a PCR reaction or other nucleic acid amplification process (e.g., ligase chain reaction (LCR), nucleic acid sequence based amplification (NASBA), transcription-mediated amplification (TMA), Q-beta amplification, strand displacement amplification, or target mediated amplification). Amplicons may comprise RNA or DNA depending on the technique used for amplification. For example, DNA amplicons may be generated by RT-PCR, whereas RNA amplicons may be generated by TMA/NASBA.

The terms "hybridize" and "hybridization" refer to the formation of complexes between nucleotide sequences which are sufficiently complementary to form complexes via Watson-Crick base pairing. Where a primer "hybridizes" with target (template), such complexes (or hybrids) are sufficiently stable to serve the priming function required by, e.g., the DNA polymerase to initiate DNA synthesis.

It will be appreciated that the hybridizing sequences need not have perfect complementarity to provide stable hybrids. In many situations, stable hybrids will form where fewer than about 10% of the bases are mismatches, ignoring loops of four or more nucleotides. Accordingly, as used herein the term "complementary" refers to an oligonucleotide that forms a stable duplex with its "complement" under assay conditions, generally where there is about 90% or greater homology.

As used herein, the term "probe" or "oligonucleotide probe" refers to a polynucleotide, as defined above, that contains a nucleic acid sequence complementary to a nucleic acid sequence present in the target nucleic acid analyte. The polynucleotide regions of probes may be composed of DNA, and/or RNA, and/or synthetic nucleotide analogs. Probes may be labeled in order to detect the target sequence. Such a label may be present at the 5' end, at the 3' end, at both the 5' and 3' ends, and/or internally. The "oligonucleotide probe" may contain at least one fluorescer and at least one quencher. Quenching of fluorophore fluorescence may be eliminated by exonuclease cleavage of the fluorophore from the oligonucleotide (e.g., TaqMan assay) or by hybridization of the oligonucleotide probe to the nucleic acid target sequence (e.g., molecular beacons). Additionally, the oligonucleotide probe will typically be derived from a sequence that lies between the sense and the antisense primers when used in a nucleic acid amplification assay.

The terms "selectively amplifies" refer to the amplification of oligonucleotides using primers that are capable of amplifying a particular oligonucleotide or subset of oligonucleotides in a mixture, but do not amplify other oligonucleotides under appropriate hybridization conditions.

As used herein, the term "recombination target site" denotes a region of a nucleic acid molecule comprising a binding site or sequence-specific motif recognized by a site-specific recombinase that binds at the target site and catalyzes recombination of specific sequences of DNA at the target site. Site-specific recombinases catalyze recombination between two such target sites. The relative orientation of the target sites determines the outcome of recombination. For example, translocation occurs if the recombination target sites are on separate DNA molecules.

As used herein, the terms "label" and "detectable label" refer to a molecule capable of detection, including, but not limited to, radioactive isotopes, fluorescers, chemiluminescers, chromophores, enzymes, enzyme substrates, enzyme cofactors, enzyme inhibitors, semiconductor nanoparticles, dyes, metal ions, metal sols, ligands (e.g., biotin, strepavidin or haptens) and the like. The term "fluorescer" refers to a substance or a portion thereof which is capable of exhibiting fluorescence in the detectable range. Particular examples of labels which may be used in the practice of the invention include, but are not limited to, Cy-3, Cy-5, SYBR green, SYBR gold, fluorescein, carboxyfluorescein (FAM), CAL Fluor Orange 560, CAL Fluor Red 610, Quasar Blue 670, tetramethyl rhodamine (TAMRA), 2',4',5',7'-tetrachloro-4-7-dichlorofluorescein (TET), FITC, rhodamine, dansyl, umbelliferone, dimethyl acridinium ester (DMAE), Texas red, luminol, NADPH, horseradish peroxidase (HRP), and α-β-galactosidase.

A "vector" is capable of transferring nucleic acid sequences to target cells (e.g., viral vectors, non-viral vectors, particulate carriers, and liposomes). Typically, "vector construct," "expression vector," and "gene transfer vector," mean any nucleic acid construct capable of directing the expression of a nucleic acid of interest and which can transfer nucleic acid sequences (e.g., oligonucleotides) to target cells. Thus, the term includes cloning and expression vehicles, as well as viral vectors.

The term "transformation" refers to the insertion of an exogenous oligonucleotide or polynucleotide into a host cell, irrespective of the method used for the insertion. For example, direct uptake, transduction or f-mating are included. The exogenous oligonucleotide or polynucleotide may be maintained as a non-integrated vector, for example, a plasmid, or alternatively, may be integrated into the host genome.

"Recombinant host cells," "host cells," "cells," "cell lines," "cell cultures," and other such terms denoting microorganisms or higher eukaryotic cell lines cultured as unicellular entities refer to cells which can be, or have been, used as recipients for oligonucleotides, recombinant vectors or other transferred DNA, and include the original progeny of the original cell which has been transfected.

The term "transfection" is used to refer to the uptake of foreign DNA by a cell. A cell has been "transfected" when exogenous DNA has been introduced inside the cell membrane. A number of transfection techniques are generally known in the art. See, e.g., Graham et al. (1973) Virology, 52:456, Sambrook et al. (2001) Molecular Cloning, a laboratory manual, 3rd edition, Cold Spring Harbor Laboratories, New York, Davis et al. (1995) Basic Methods in Molecular Biology, 2nd edition, McGraw-Hill, and Chu et al. (1981) Gene 13:197. Such techniques can be used to introduce one or more exogenous DNA moieties into suitable host cells. The term refers to both stable and transient uptake of the genetic material.

"Substantially purified" generally refers to isolation of a substance (compound, oligonucleotide, polynucleotide, protein, or polypeptide) such that the substance comprises the majority percent of the sample in which it resides. Typically in a sample, a substantially purified component comprises 50%, preferably 80%-85%, more preferably 90-95% of the sample. Techniques for purifying oligonucleotides, polynucleotides, and polypeptides of interest are well-known in the art and include, for example, ion-exchange chromatography, affinity chromatography and sedimentation according to density.

By "isolated" is meant, when referring to a polypeptide, that the indicated molecule is separate and discrete from the whole organism with which the molecule is found in nature or is present in the substantial absence of other biological macro-molecules of the same type. The term "isolated" with respect to a polynucleotide or oligonucleotide is a nucleic acid molecule devoid, in whole or part, of sequences normally associated with it in nature; or a sequence, as it exists in nature, but having heterologous sequences in association therewith; or a molecule disassociated from the chromosome.

"Homology" refers to the percent identity between two polynucleotide or two polypeptide molecules. Two nucleic acid, or two polypeptide sequences are "substantially homologous" to each other when the sequences exhibit at least about 50% sequence identity, preferably at least about 75% sequence identity, more preferably at least about 80%-85% sequence identity, more preferably at least about 90% sequence identity, and most preferably at least about 95%-98% sequence identity over a defined length of the molecules. As used herein, substantially homologous also refers to sequences showing complete identity to the specified sequence.

In general, "identity" refers to an exact nucleotide-to-nucleotide or amino acid-to-amino acid correspondence of two oligonucleotides, polynucleotides or polypeptide sequences, respectively. Percent identity can be determined by a direct comparison of the sequence information between two molecules by aligning the sequences, counting the exact number of matches between the two aligned sequences, dividing by the length of the shorter sequence, and multiplying the result by 100. Readily available computer programs can be used to aid in the analysis, such as ALIGN, Dayhoff, M. O. in *Atlas of Protein Sequence and Structure* M. O. Dayhoff ed., 5 Suppl. 3:353-358, National biomedical Research Foundation, Washington, D.C., which adapts the local homology algorithm of Smith and Waterman *Advances in Appl. Math.* 2:482-489, 1981 for peptide analysis. Programs for determining nucleotide sequence identity are available in the Wisconsin Sequence Analysis Package, Version 8 (available from Genetics Computer Group, Madison, Wis.) for example, the BESTFIT, FASTA and GAP programs, which also rely on the Smith and Waterman algorithm. These programs are readily utilized with the default parameters recommended by the manufacturer and described in the Wisconsin Sequence Analysis Package referred to above. For example, percent identity of a particular nucleotide sequence to a reference sequence can be determined using the homology algorithm of Smith and Waterman with a default scoring table and a gap penalty of six nucleotide positions.

Another method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs are readily available.

Alternatively, homology can be determined by hybridization of polynucleotides under conditions which form stable duplexes between homologous regions, followed by digestion with single-stranded-specific nuclease(s), and size determination of the digested fragments. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; *DNA Cloning, supra; Nucleic Acid Hybridization, supra.*

2. MODES OF CARRYING OUT THE INVENTION

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting.

Although a number of methods and materials similar or equivalent to those described herein can be used in the practice of the present invention, the preferred materials and methods are described herein.

The present invention relates to a simple, affordable, and scalable method that allows sequence-verified, oligonucleotide DNA to be easily isolated from complex libraries. In particular, the inventors developed a method utilizing a selectable system for combining DNA sequences in yeast, mating of yeast clones in high-density ordered arrays, and high throughput sequencing (see Examples 1-4).

In order to further an understanding of the invention, a more detailed discussion is provided below regarding methods of isolating sequence-verified, oligonucleotides from mixtures and libraries.

A. Sequence-Verification of Oligonucleotides

In one aspect, the invention includes a method for isolating a sequence-verified oligonucleotide from a composition comprising a mixture of oligonucleotides (e.g., oligonucleotide library or pooled mixture). The method comprises: a) providing the composition comprising the mixture of oligonucleotides, wherein each oligonucleotide comprises an unknown sequence and common priming sites for amplification; b) amplifying one or more oligonucleotides; c) transforming a plurality of host cells with the amplified oligonucleotides; d) plating the plurality of transformed host cells in an ordered array on media suitable for growth of the host cells; e) culturing the plurality of transformed host cells under conditions whereby each host cell produces a colony of clones in the ordered array; f) introducing an oligonucleotide from a colony in the ordered array into a barcoder cell, wherein the barcoder cell comprises a nucleic acid comprising a recombination target site for a site-specific recombinase and a barcode sequence that identifies the colony in the ordered array to which the oligonucleotide corresponds; g) translocating the oligonucleotide to a position adjacent to the barcode sequence of the barcoder cell using a site-specific recombinase system, wherein site-specific recombination with the recombination target site of the barcoder cell generates a nucleic acid comprising a barcode-oligonucleotide fusion sequence; h) sequencing the barcode-oligonucleotide fusion sequence to identify a colony in the ordered array comprising a sequence-verified oligonucleotide; i) picking a clone comprising the sequence-verified oligonucleotide from the colony in the ordered array identified by the barcode; and j) isolating the sequence-verified oligonucleotide from the clone.

In particular, the methods of the invention are applicable to oligonucleotides synthesized on chips, which often have high error rates or other methods of oligonucleotide synthesis in solution or on solid phase that produce pooled mixtures of high chemical complexity. Oligonucleotides are commonly synthesized, for example, on solid phase via phosphoramidite chemistry, as disclosed in U.S. Pat. Nos. 4,458,066 and 4,415,732, incorporated herein by reference; Beaucage et al., *Tetrahedron* (1992) 48:2223-2311; and Applied Biosystems User Bulletin No. 13 (1 Apr. 1987). Other chemical synthesis methods include, for example, the phosphotriester method described by Narang et al., *Meth. Enzymol.* (1979) 68:90-98 and the phosphodiester method disclosed by Brown et al., *Meth. Enzymol.* (1979) 68:109-151.

In certain embodiments, oligonucleotides are integrated into the genome of a host cell at a target locus. For example, a targeting sequence may be added to each oligonucleotide, wherein the targeting sequence is sufficiently homologous to a genomic target locus of the host cell such that the oligonucleotide integrates into the genome at the target locus in the transformed host cell by homologous recombination. In one embodiment, the oligonucleotides are amplified with a primer comprising an integration targeting sequence that is sufficiently homologous to a genomic target locus of the host cell such that amplicons of the oligonucleotides integrate into the genome at the target locus in the transformed host cell by homologous recombination. In order to facilitate genomic integration at the target locus, a host cell may also be transformed with a recombinant polynucleotide encoding a restriction enzyme operably linked to a promotor, wherein the restriction enzyme creates a double strand break at the genomic target locus that assists homologous recombination. In addition, a selectable marker may be used that selects for clones that have undergone successful integration of an oligonucleotide at the genomic target locus.

In other embodiments, oligonucleotides are integrated into a plasmid of a host cell at a particular target locus. For example, a plasmid targeting sequence may be added to each oligonucleotide, wherein the targeting sequence is sufficiently homologous to a target locus on a plasmid in the host cell, such that the oligonucleotide integrates into the plasmid at the target locus in the transformed host cell. In one embodiment, the oligonucleotides are amplified with a primer comprising a targeting sequence that is sufficiently homologous to a target locus on a plasmid in the host cell, such that the oligonucleotide amplicons integrate into the plasmid at the target locus in the transformed host cell. In order to facilitate integration at the plasmid target locus, a host cell may also be transformed with a recombinant polynucleotide encoding a restriction enzyme operably linked to a promotor, wherein the restriction enzyme creates a double strand break at the plasmid target locus that assists homologous recombination. In addition, a selectable marker may be used that selects for clones that have undergone successful integration of an oligonucleotide at the plasmid target locus.

In another embodiment, the oligonucleotides are provided in vectors for transformation of the host cells. In one embodiment, the unknown sequence of each oligonucleotide is flanked by a common 5' restriction site and a common 3' restriction site. The method further comprises performing a restriction digest that selectively cleaves each oligonucleotide at the common 5' restriction site and the common 3' restriction site to produce restriction fragments, which can be cloned into vectors (e.g., plasmids or viral vectors). The plurality of host cells is then transformed with the vectors comprising the oligonucleotides.

In addition, adapter sequences can be added to oligonucleotides to facilitate high-throughput amplification or sequencing. For example, a pair of adapter sequences can be added at the 5' and 3' ends of an oligonucleotide to allow amplification or sequencing of multiple oligonucleotides simultaneously by the same set of primers. Additionally, restriction sites can be incorporated into oligonucleotides to facilitate cloning of oligonucleotides into vectors.

The recipient host cells that are transformed with the oligonucleotides may be prokaryotic cells or eukaryotic cells. Recipient host cells are preferably designed for high-efficiency incorporation of oligonucleotide libraries by transformation. Methods of introducing oligonucleotides (or exogenous nucleic acids) into a host cell are well known in the art. Commonly used methods of transformation include chemically induced transformation, typically using divalent cations (e.g., $CaCl_2$), and electroporation. See, e.g., Sambrook et al. (2001) Molecular Cloning, a laboratory manual, $3^{rd}$ edition, Cold Spring Harbor Laboratories, New York, Davis et al. (1995) Basic Methods in Molecular Biology, $2^{nd}$ edition, McGraw-Hill, and Chu et al. (1981) Gene 13:197; herein incorporated by reference in their entireties.

Figure 3A:
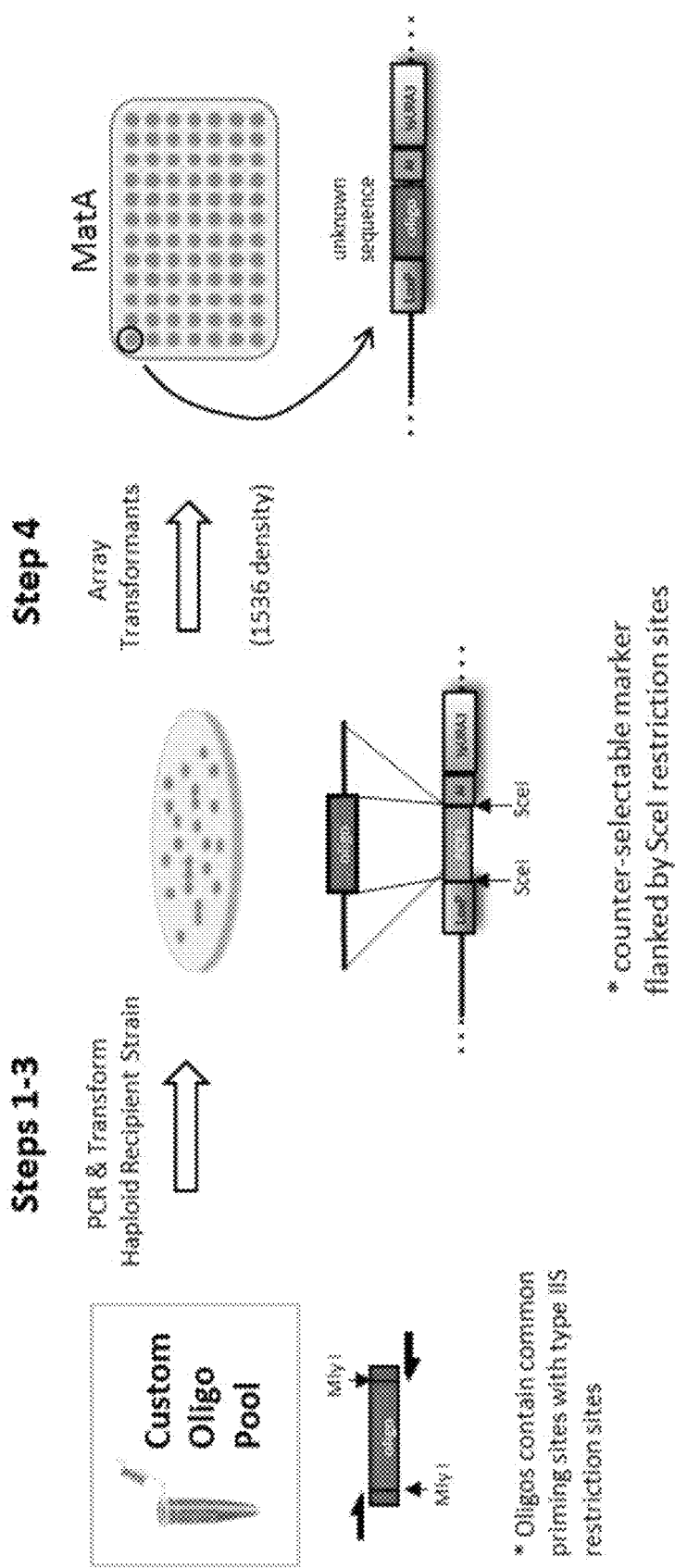
Figure 3B:
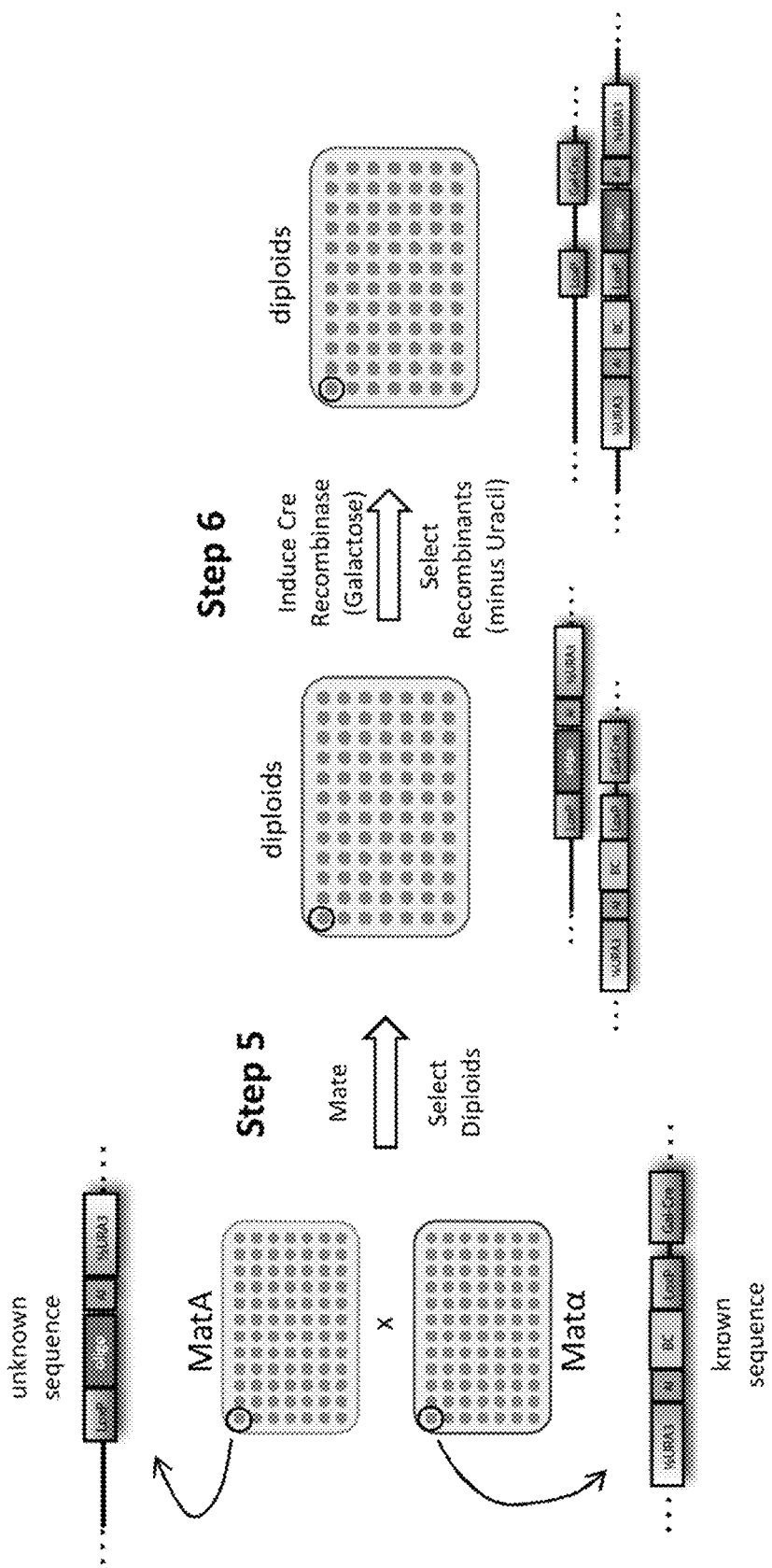
Figure 3E:
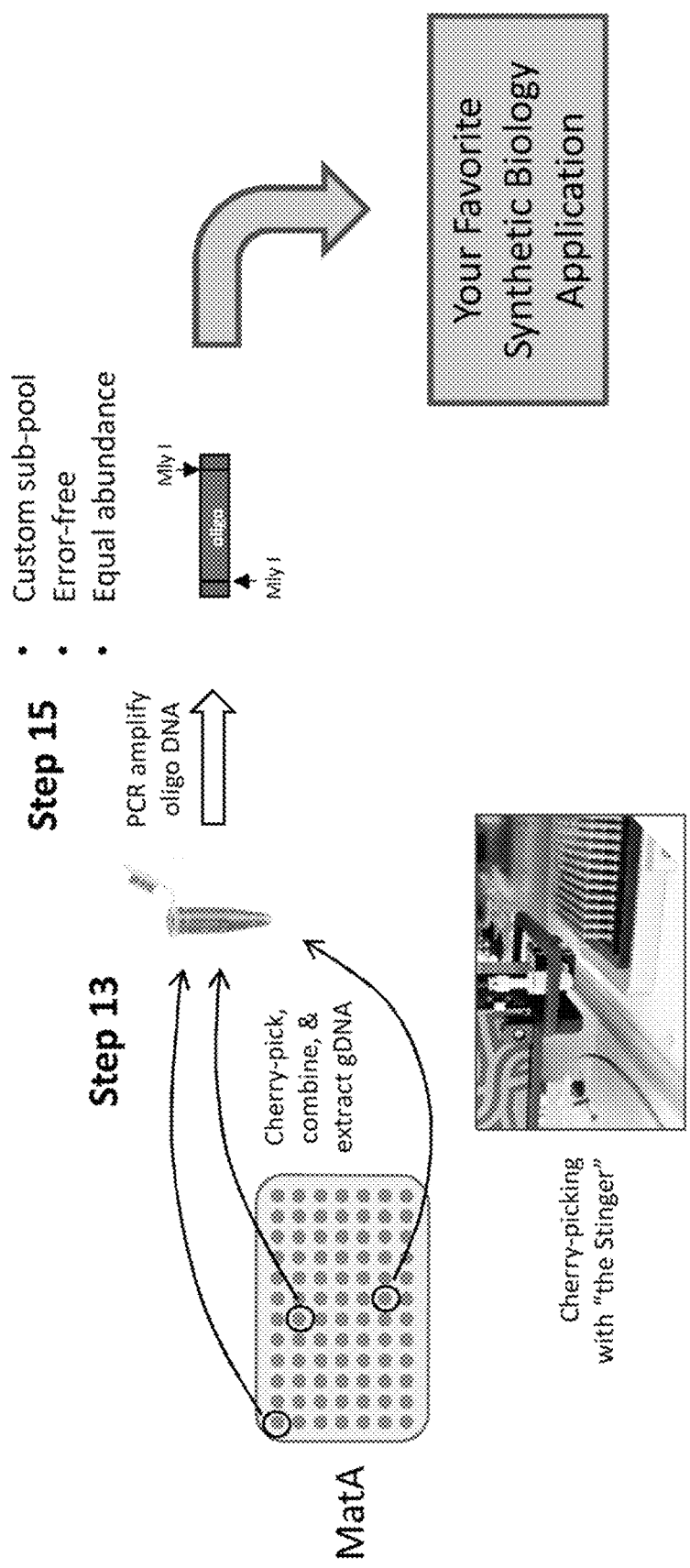
Figure 4:
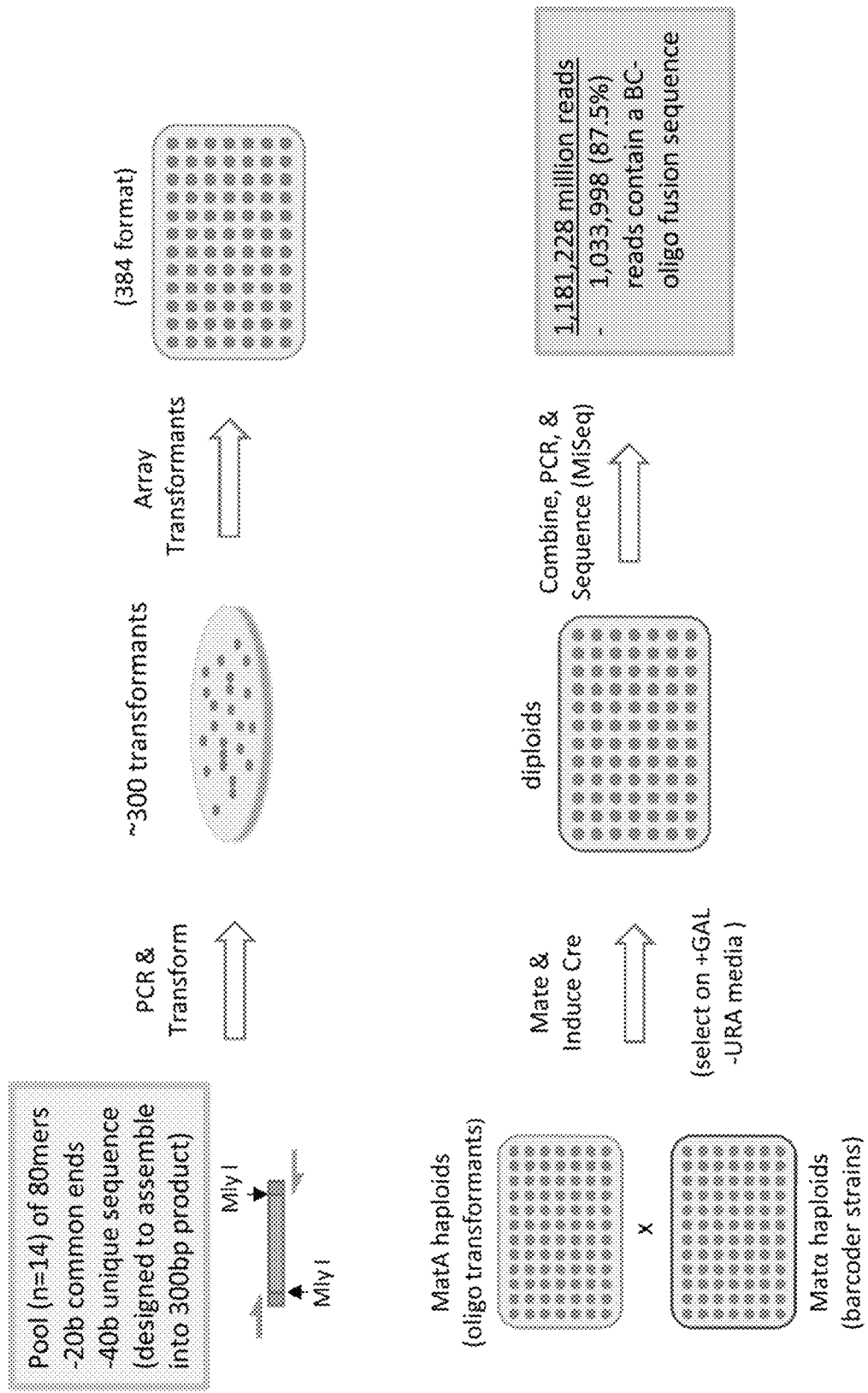
FIG. 4 shows a schematic for the First Pilot Experiment (Gene Assembly). Sequence-verified oligonucleotides were isolated from a pooled mixture of oligonucleotides (fourteen 80mers comprising common ends and 40 bases of unique sequence) and assembled into a 300 base pair product.
Figure 5:
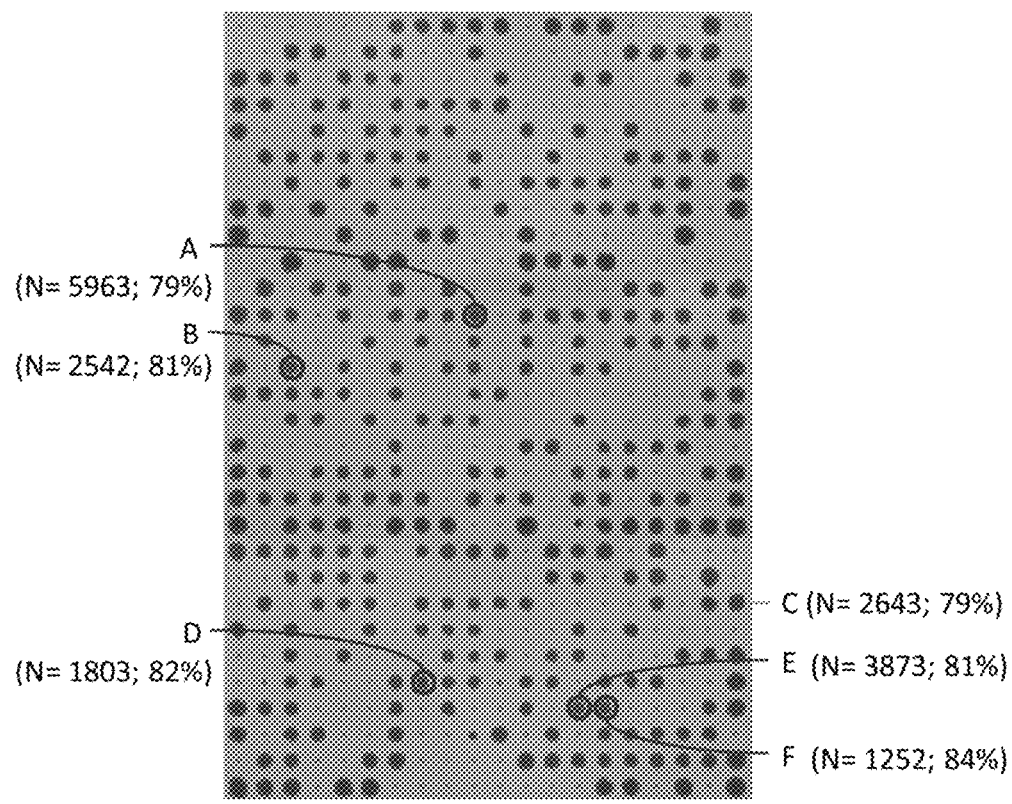
FIG. 5 shows the identification of oligonucleotide synthesis errors. Sequence verification of clones identifies clones having sequence errors (SEQ ID NO:13) and clones having the correct sequence (SEQ ID NO:14).

Barcoder cells are used for high-throughput tagging of the oligonucleotides incorporated into the recipient host cells. The barcode sequences are used to identify the colonies from which each oligonucleotide originated. The use of barcodes allows oligonucleotides from different cells to be pooled in a single reaction mixture for sequencing while still being able to trace back a particular oligonucleotide to the colony from which it originated. Each cell is identified by a unique barcode sequence comprising at least five nucleotides. A barcode sequence can be added to a nucleic acid, for example, by carrying out PCR with a primer that contains a region comprising the barcode sequence and a region that is complementary to a nucleic acid of interest such that the barcode sequence is incorporated into the final amplified nucleic acid product. Barcode sequences can be added at one or both ends of an amplicon. Exemplary barcode sequences are shown in FIG. 3C. Barcoder cells can be produced by transforming a cell with such a nucleic acid comprising a barcode. Exemplary yeast barcoder cells are described in Example 2.

In certain embodiments, recipient host cells comprising an oligonucleotide library are initially plated at separate locations in an ordered array. Barcoder cells are plated in a matching array, and oligonucleotides from each recipient host cell are introduced into each corresponding barcoder cell. This can be accomplished for example, by mating the recipient host cells and barcoder cells.

Example 1 describes using the yeast, *Saccharomyces cerevisiae*, for this purpose. *Saccharomyces cerevisiae* exists in both diploid and haploid forms. Mating only occurs between haploid forms of yeast of different mating types, which can be either the a or α mating type. The allele at the MAT locus (either MATa or MATα) determines mating type. Diploid cells result from the mating of MATa and MATα yeast strains. Thus, a haploid recipient yeast host cell comprising an oligonucleotide can be mated with a haploid barcoder yeast cell to produce a diploid yeast cell comprising both the oligonucleotide sequence and the barcode sequence on separate nucleic acids. For example, recipient yeast host cells of strain MATα can be mated with barcoder yeast cells of strain MATa. Alternatively, recipient yeast host cells of strain MATa can be mated with barcoder yeast cells of strain MATα.

Translocation of an oligonucleotide sequence to a position adjacent to a barcode sequence in order to tag the oligonucleotide with the barcode may be accomplished with any suitable site-specific recombinase system. Site-specific recombinases catalyze DNA exchange reactions between two recombination target sites. A "recombination target site" is a region of a nucleic acid molecule, typically 30-50 nucleotides in length, comprising a binding site or sequence-specific motif recognized by the site-specific recombinase. Upon binding to the target site, the site-specific recombinase catalyzes recombination of specific sequences of DNA at the target site. The relative orientation of the target sites determines the outcome of recombination, which can result in excision, insertion, inversion, translocation or cassette exchange. Translocation occurs if the recombination target sites are on separate DNA molecules. Site-specific recombinase systems often include tyrosine recombinases or serine recombinases, but other types of site-specific recombinases may also be used along with their specific recombination target sites. Exemplary site-specific recombinase systems include Cre-loxP, Flp-FRT, PhiC31-att, and Dre-rox site-specific recombinase systems. For a description of these and other site-specific recombinase systems that can be used in the practice of the invention, see, e.g., Wirth et al. (2007) Curr. Opin. Biotechnol. 18(5):411-419; Branda et al. (2004) Dev. Cell 6(1):7-28; Birling et al. (2009) Methods Mol. Biol. 561:245-263; Bucholtz et al. (2008) J. Vis. Exp. May 29 (15) pii: 718; Nern et al. (2011) Proc. Natl. Acad. Sci. U.S.A. 108(34):14198-14203; Smith et al. (2010) Biochem. Soc. Trans. 38(2):388-394; Turan et al. (2011) FASEB J. 25(12): 4088-4107; Garcia-Otin et al. (2006) Front. Biosci. 11:1108-1136; Gaj et al. (2014) Biotechnol Bioeng. 111(1):1-15; Krappmann (2014) Appl. Microbiol. Biotechnol. 98(5): 1971-1982; Kolb et al. (2002) Cloning Stem Cells 4(1):65-80; and Lopatniuk et al. (2015) J. Appl. Genet. 56(4):547-550; herein incorporated by reference in their entireties.

A recombination target site for a site-specific recombinase can be linked to an oligonucleotide in a number of ways. For example, an oligonucleotide can be amplified with a primer comprising a recombination target site capable of undergoing recombination with the recombination target site of a barcoder cell. Alternatively, an oligonucleotide can be integrated into the genome or a plasmid of a host cell at a locus adjacent to a recombination target site capable of undergoing recombination with the recombination target site of a barcoder cell to produce a barcode-oligonucleotide fusion sequence. In addition, a selectable marker may be used that selects for clones that have undergone successful site-specific recombination.

Amplification of oligonucleotides may be performed before transformation of cells with oligonucleotides or after isolation of sequence verified oligonucleotides. Any method for amplifying oligonucleotides may be used, including, but not limited to polymerase chain reaction (PCR), nucleic acid sequence-based amplification (NASBA), transcription mediated amplification (TMA), strand displacement amplification (SDA), and ligase chain reaction (LCR). In one embodiment, the oligonucleotides comprise common 5' and 3' priming sites to allow amplification of the oligonucleotides in parallel with a set of universal primers. In another embodiment, a set of selective primers is used to selectively amplify a subset of the oligonucleotides from a mixture.

PCR is a technique for amplifying a desired target nucleic acid sequence contained in a nucleic acid molecule or mixture of molecules. In PCR, a pair of primers is employed in excess to hybridize to the complementary strands of the target nucleic acid. The primers are each extended by a polymerase using the target nucleic acid as a template. The extension products become target sequences themselves after dissociation from the original target strand. New primers are then hybridized and extended by a polymerase, and the cycle is repeated to geometrically increase the number of target sequence molecules. The PCR method for amplifying target nucleic acid sequences in a sample is well known in the art and has been described in, e.g., Innis et al. (eds.) *PCR Protocols* (Academic Press, N Y 1990); Taylor (1991) *Polymerase chain reaction: basic principles and automation, in PCR: A Practical Approach*, McPherson et al. (eds.) IRL Press, Oxford; Saiki et al. (1986) *Nature* 324:163; as well as in U.S. Pat. Nos. 4,683,195, 4,683,202 and 4,889, 818, all incorporated herein by reference in their entireties.

In particular, PCR uses relatively short oligonucleotide primers which flank the target nucleotide sequence to be amplified, oriented such that their 3' ends face each other, each primer extending toward the other. The polynucleotide sample is extracted and denatured, preferably by heat, and hybridized with first and second primers that are present in molar excess. Polymerization is catalyzed in the presence of the four deoxyribonucleotide triphosphates (dNTPs—dATP, dGTP, dCTP and dTTP) using a primer- and template-dependent polynucleotide polymerizing agent, such as any enzyme capable of producing primer extension products, for example, *E. coli* DNA polymerase I, Klenow fragment of DNA polymerase I, T4 DNA polymerase, thermostable DNA polymerases isolated from *Thermus aquaticus* (Taq), available from a variety of sources (for example, Perkin Elmer), *Thermus thermophilus* (United States Biochemicals), *Bacillus stereothermophilus* (Bio-Rad), or *Thermococcus litoralis* ("Vent" polymerase, New England Biolabs). This results in two "long products" which contain the respective primers at their 5' ends covalently linked to the newly synthesized complements of the original strands. The reaction mixture is then returned to polymerizing conditions, e.g., by lowering the temperature, inactivating a denaturing agent, or adding more polymerase, and a second cycle is initiated. The second cycle provides the two original strands, the two long products from the first cycle, two new long products replicated from the original strands, and two "short products" replicated from the long products. The short products have the sequence of the target sequence with a primer at each end. On each additional cycle, an additional two long products are produced, and a number of short products equal to the number of long and short products remaining at the end of the previous cycle. Thus, the number of short products containing the target sequence grows exponentially with each cycle. Preferably, PCR is carried out with a commercially available thermal cycler, e.g., Perkin Elmer.

RNAs may be amplified by reverse transcribing the RNA into cDNA, and then performing PCR (RT-PCR), as described above. Alternatively, a single enzyme may be used for both steps as described in U.S. Pat. No. 5,322,770, incorporated herein by reference in its entirety. RNA may also be reverse transcribed into cDNA, followed by asymmetric gap ligase chain reaction (RT-AGLCR) as described by Marshall et al. (1994) *PCR Meth. App.* 4:80-84.

Nucleic acid sequence based amplification (NASBA) is an isothermal RNA-specific amplification method that does not require thermal cycling instrumentation. RNA is initially reverse transcribed such that the single-stranded RNA target is copied into a double-stranded DNA molecule that serves as a template for RNA transcription. Detection of the amplified RNA is typically accomplished either by electrochemi-luminescence or in real-time, for example, with fluorescently labeled molecular beacon probes. See, e.g., Lau et al. (2006) Dev. Biol. (Basel) 126:7-15; and Deiman et al. (2002) Mol. Biotechnol. 20(2):163-179.

The Ligase Chain Reaction (LCR) is an alternate method for nucleic acid amplification. In LCR, probe pairs are used which include two primary (first and second) and two secondary (third and fourth) probes, all of which are employed in molar excess to the target. The first probe hybridizes to a first segment of the target strand, and the second probe hybridizes to a second segment of the target strand, the first and second segments being contiguous so that the primary probes abut one another in 5' phosphate-3' hydroxyl relationship, and so that a ligase can covalently fuse or ligate the two probes into a fused product. In addition, a third (secondary) probe can hybridize to a portion of the first probe and a fourth (secondary) probe can hybrid-ize to a portion of the second probe in a similar abutting fashion. If the target is initially double stranded, the secondary probes also will hybridize to the target complement in the first instance. Once the ligated strand of primary probes is separated from the target strand, it will hybridize with the third and fourth probes which can be ligated to form a complementary, secondary ligated product. It is important to realize that the ligated products are functionally equivalent to either the target or its complement. By repeated cycles of hybridization and ligation, amplification of the target sequence is achieved. This technique is described more completely in EPA 320,308 to K. Backman published Jun. 16, 1989 and EPA 439,182 to K. Backman et al., published Jul. 31, 1991, both of which are incorporated herein by reference.

Other known methods for amplification of nucleic acids include, but are not limited to self-sustained sequence replication (3SR) described by Guatelli et al., *Proc. Mid Acad. Sci. USA* (1990) 87:1874-1878 and J. Compton, *Nature* (1991) 350:91-92 (1991); Q-beta amplification; strand displacement amplification (as described in Walker et al., *Clin. Chem.* (1996) 42:9-13 and EPA 684,315; target mediated amplification, as described in International Publication No. WO 93/22461, and the TaqMan assay.

B. Sequencing of Oligonucleotide-Barcode Fusions

Any high-throughput technique for sequencing can be used in the practice of the invention. DNA sequencing techniques include dideoxy sequencing reactions (Sanger method) using labeled terminators or primers and gel separation in slab or capillary, sequencing by synthesis using reversibly terminated labeled nucleotides, pyrosequencing, 454 sequencing, sequencing by synthesis using allele specific hybridization to a library of labeled clones followed by ligation, real time monitoring of the incorporation of labeled nucleotides during a polymerization step, polony sequencing, SOLID sequencing, and the like.

Certain high-throughput methods of sequencing comprise a step in which individual molecules are spatially isolated on a solid surface where they are sequenced in parallel. Such solid surfaces may include nonporous surfaces (such as in Solexa sequencing, e.g. Bentley et al, Nature, 456: 53-59 (2008) or Complete Genomics sequencing, e.g. Drmanac et al, Science, 327: 78-81 (2010)), arrays of wells, which may include bead- or particle-bound templates (such as with 454, e.g. Margulies et al, Nature, 437: 376-380 (2005) or Ion Torrent sequencing, U.S. patent publication 2010/0137143 or 2010/0304982), micromachined membranes (such as with SMRT sequencing, e.g. Eid et al, Science, 323: 133-138 (2009)), or bead arrays (as with SOLiD sequencing or polony sequencing, e.g. Kim et al, Science, 316: 1481-1414 (2007)). Such methods may comprise amplifying the isolated molecules either before or after they are spatially isolated on a solid surface. Prior amplification may comprise emulsion-based amplification, such as emulsion PCR, or rolling circle amplification.

Of particular interest is sequencing on the Illumina MiSeq platform, which uses reversible-terminator sequencing by synthesis technology (see, e.g., Shen et al. (2012) BMC Bioinformatics 13:160; Junemann et al. (2013) Nat. Biotechnol. 31(4):294-296; Glenn (2011) Mol. Ecol. Resour. 11(5):759-769; Thudi et al. (2012) Brief Funct. Genomics 11(1):3-11; herein incorporated by reference).

These sequencing approaches can thus be used to sequence the barcode-oligonucleotide fusion sequences to verify the sequence of an oligonucleotide and identify its corresponding colony in an ordered array. Short DNA barcodes can also be used in multiplex sequencing of ordered array samples. Accordingly, a clone comprising any desired sequence-verified oligonucleotide can then be picked out of an ordered array of cells (e.g., with an automated robotic device or manually). If desired, the isolated oligonucleotide can be amplified and purified for use in downstream applications.

C. Kits

The above-described reagents, including recipient cells, barcoder cells, media suitable for growing recipient cells and barcoder cells, and site-specific recombinase systems can be provided in kits, with suitable instructions and other necessary reagents, in order to isolate sequence-verified oligonucleotides from a mixture or library, as described above. The kit will normally contain in separate containers the recipient cells and barcoder cells and other reagents that the method requires. Instructions (e.g., written, CD-ROM, DVD, etc.) for carrying out the procedure usually will be included in the kit. The kit can also contain other packaged reagents and materials (e.g., transfection agents, reagents for performing nucleic acid amplification, such as by PCR, buffers, and the like). Oligonucleotide libraries can be processed to provide sequence-verified oligonucleotides as described herein using these kits.

D. Applications

Sequence-verified oligonucleotides can be used, for example, as probes for hybridization-based detection, primers for amplification of nucleic acids or sequencing (e.g., primer libraries for gene expression detection or quantification), or as templates for making small interfering RNAs (siRNAs) or guide RNAs. Additionally, sequence-verified oligonucleotides can be used in various applications, including, but not limited to, CRISPR interference (CRISPRi), SNP genotyping, metagenomics, protein and antibody engineering, allele replacement, gene synthesis, pathway synthesis (e.g., biofuels, new drugs), or genome synthesis.

In particular, the methods of the invention can be used to remove oligonucleotides with errors from libraries or contaminating oligonucleotides from pooled mixtures after synthesis. By collecting clones comprising sequence-verified oligonucleotides, new essentially error-free libraries (e.g., probe library or a primer library) can be created. Colonies comprising sequence-verified oligonucleotides can be arranged in ordered arrays to allow ready picking of clones comprising any individual oligonucleotide or subset of oligonucleotides on-demand.

Additionally, the methods of the invention are useful for in vitro gene synthesis. In particular, the methods are applicable to gene assembly from oligonucleotides synthesized on chips, which often have high error rates, or other methods of oligonucleotide synthesis in solution or on solid phase that produce pooled mixtures of high chemical complexity. Sequence-verified oligonucleotides collectively comprising all or most of the sequence of a gene can be isolated, as described herein, to construct a gene or portion of a gene. Gene assembly may be performed using methods well known in the art, including, for example, ligase chain reaction (LCR) or assembly PCR.

In particular, sequence-verified oligonucleotides can be used as probes for hybridization-based detection methods. Such probes will find use in various applications in scientific research, medicine, and forensics, including but not limited to, Northern or Southern blot analysis, genotyping, and expression profiling. Probes can be used, for example, for detection of PCR amplicons, SNPs, short tandem repeats (microsatellite) regions, and restriction fragment length polymorphism (RFLP).

When utilizing a hybridization-based detection system, an oligonucleotide probe is chosen that is complementary to a target nucleic acid sequence. By selection of appropriate conditions, the probe and the target sequence "selectively hybridize," or bind, to each other to form a hybrid molecule. An oligonucleotide that "selectively hybridizes" to a particular target sequence under hybridization conditions described below, denotes an oligonucleotide that binds to the target nucleic acid analyte, but does not bind to a sequence from non-target analytes.

In one embodiment, a nucleic acid molecule is capable of hybridizing selectively to a target sequence under moderately stringent hybridization conditions. Moderately stringent hybridization conditions allow detection of a target nucleic acid sequence of at least 14 nucleotides in length having at least approximately 70% sequence identity with the sequence of the selected nucleic acid probe. In another embodiment, such selective hybridization is performed under stringent hybridization conditions. Stringent hybridization conditions allow detection of target nucleic acid sequences of at least 14 nucleotides in length having a sequence identity of greater than 90% with the sequence of the selected nucleic acid probe. Hybridization conditions useful for probe/target hybridization where the probe and target have a specific degree of sequence identity, can be determined as is known in the art (see, for example, *Nucleic Acid Hybridization: A Practical Approach*, editors B. D. Hames and S. J. Higgins, (1985) Oxford; Washington, D.C.; IRL Press). Hybrid molecules can be formed, for example, on a solid support, in solution, and in tissue sections. The formation of hybrids can be monitored by inclusion of a reporter molecule, typically, in the probe. Such reporter molecules or detectable labels include, but are not limited to, radioactive elements, fluorescent markers, and molecules to which an enzyme-conjugated ligand can bind.

With respect to stringency conditions for hybridization, it is well known in the art that numerous equivalent conditions can be employed to establish a particular stringency by varying, for example, the following factors: the length and nature of probe and target sequences, base composition of the various sequences, concentrations of salts and other hybridization solution components, the presence or absence of blocking agents in the hybridization solutions (e.g., formamide, dextran sulfate, and polyethylene glycol), hybridization reaction temperature and time parameters, as well as, varying wash conditions. The selection of a particular set of hybridization conditions is well known (see, for example, Sambrook, et al., *Molecular Cloning: A Laboratory Manual*, 3rd Edition, 2001).

Oligonucleotides, particularly probe oligonucleotides, may be coupled to labels for detection. There are several means known for derivatizing oligonucleotides with reactive functionalities which permit the addition of a label. For example, several approaches are available for biotinylating probes so that radioactive, fluorescent, chemiluminescent, enzymatic, or electron dense labels can be attached via avidin. See, e.g., Broken et al., *Nucl. Acids Res.* (1978) 5:363-384 which discloses the use of ferritin-avidin-biotin labels; and Chollet et al., *Nucl. Acids Res.* (1985) 13:1529-1541 which discloses biotinylation of the 5' termini of oligonucleotides via an aminoalkylphosphoramide linker arm. Several methods are also available for synthesizing amino-derivatized oligonucleotides which are readily labeled by fluorescent or other types of compounds derivatized by amino-reactive groups, such as isothiocyanate, N-hydroxysuccinimide, or the like, see, e.g., Connolly, *Nucl. Acids Res.* (1987) 15:3131-3139, Gibson et al. *Nucl. Acids*

Res. (1987) 15:6455-6467 and U.S. Pat. No. 4,605,735 to Miyoshi et al. Methods are also available for synthesizing sulfhydryl-derivatized oligonucleotides, which can be reacted with thiol-specific labels, see, e.g., U.S. Pat. No. 4,757,141 to Fung et al., Connolly et al., *Nucl. Acids Res.* (1985) 13:4485-4502 and Spoat et al. *Nucl. Acids Res.* (1987) 15:4837-4848. A comprehensive review of methodologies for labeling DNA fragments is provided in Matthews et al., *Anal. Biochem.* (1988) 169:1-25.

For example, oligonucleotides may be fluorescently labeled by linking a fluorescent molecule to the non-ligating terminus of the molecule. Guidance for selecting appropriate fluorescent labels can be found in Smith et al., *Meth. Enzymol.* (1987) 155:260-301; Karger et al., *Nucl. Acids Res.* (1991) 19:4955-4962; Guo et al. (2012) Anal. Bioanal. Chem. 402(10):3115-3125; and *Molecular Probes Handbook, A Guide to Fluorescent Probes and Labeling Technologies*, 11$^{th}$ edition, Johnson and Spence eds., 2010 (Molecular Probes/Life Technologies). Fluorescent labels include fluorescein and derivatives thereof, such as disclosed in U.S. Pat. No. 4,318,846 and Lee et al., *Cytometry* (1989) 10:151-164. Dyes for use in the present invention include 3-phenyl-7-isocyanatocoumarin, acridines, such as 9-isothiocyanatoacridine and acridine orange, pyrenes, benzoxadiazoles, and stilbenes, such as disclosed in U.S. Pat. No. 4,174,384. Additional dyes include SYBR green, SYBR gold, Yakima Yellow, Texas Red, 3-(ε-carboxypentyl)-3'-ethyl-5,5'-dimethyloxa-carbocyanine (CYA); 6-carboxy fluorescein (FAM); CAL Fluor Orange 560, CAL Fluor Red 610, Quasar Blue 670; 5,6-carboxyrhodamine-110 (R110); 6-carboxyrhodamine-6G (R6G); N',N',N',N'-tetramethyl-6-carboxyrhodamine (TAMRA); 6-carboxy-X-rhodamine (ROX); 2',4',5',7',-tetrachloro-4-7-dichlorofluorescein (TET); 2',7'-dimethoxy-4',5'-6 carboxyrhodamine (JOE); 6-carboxy-2',4,4',5',7,7'-hexachlorofluorescein (HEX); Dragonfly orange; ATTO-Tec; Bodipy; ALEXA; VIC, Cy3, and Cy5. These dyes are commercially available from various suppliers such as Life Technologies (Carlsbad, Calif.), Biosearch Technologies (Novato, Calif.), and Integrated DNA Technologies (Coralville, Iowa). Fluorescent labels include fluorescein and derivatives thereof, such as disclosed in U.S. Pat. No. 4,318,846 and Lee et al., *Cytometry* (1989) 10:151-164, and 6-FAM, JOE, TAMRA, ROX, HEX-1, HEX-2, ZOE, TET-1 or NAN-2, and the like.

Oligonucleotides can also be labeled with a minor groove binding (MGB) molecule, such as disclosed in U.S. Pat. Nos. 6,884,584, 5,801,155; Afonina et al. (2002) Biotechniques 32:940-944, 946-949; Lopez-Andreo et al. (2005) Anal. Biochem. 339:73-82; and Belousov et al. (2004) Hum Genomics 1:209-217. Oligonucleotides having a covalently attached MGB are more sequence specific for their complementary targets than unmodified oligonucleotides. In addition, an MGB group increases hybrid stability with complementary DNA target strands compared to unmodified oligonucleotides, allowing hybridization with shorter oligonucleotides.

Additionally, oligonucleotides can be labeled with an acridinium ester (AE) using the techniques described below. Current technologies allow the AE label to be placed at any location within the probe. See, e.g., Nelson et al., (1995) "Detection of Acridinium Esters by Chemiluminescence" in *Nonisotopic Probing, Blotting and Sequencing*, Kricka L. J. ed) Academic Press, San Diego, Calif.; Nelson et al. (1994) "Application of the Hybridization Protection Assay (HPA) to PCR" in *The Polymerase Chain Reaction*, Mullis et al. (eds.) Birkhauser, Boston, Mass.; Weeks et al., *Clin. Chem.* (1983) 29:1474-1479; Berry et al., *Clin. Chem.* (1988) 34:2087-2090. An AE molecule can be directly attached to the probe using non-nucleotide-based linker arm chemistry that allows placement of the label at any location within the probe. See, e.g., U.S. Pat. Nos. 5,585,481 and 5,185,439.

3. EXPERIMENTAL

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

Example 1

A Scalable Method for Isolation and Sequence Verification of Oligonucleotides from Complex Libraries Introduction We have developed a method that broadens the utility of inexpensive DNA oligonucleotides that are synthesized on arrays. Although inexpensive, these oligonucleotides are delivered as pools often containing mixtures of thousands of different oligonucleotides. These pools also contain many DNA molecules with errors (i.e., incorrect sequences), and the concentration of individual oligonucleotides varies widely, thereby limiting their utility.

Our method provides a scalable, inexpensive, and simple approach for isolating sequence-verified oligonucleotides from these complex mixtures. In addition, it permits normalization of individual oligonucleotide concentrations, and retrieval of subsets of individual oligonucleotides from complex libraries 'on-demand', without the need for set-specific common priming sites. The aforementioned inadequacies of current DNA synthesis platforms limit the application of synthetic DNA in biology and medicine. There are several current applications of synthetic DNA (e.g. targeted DNA sequencing, metagenomic profiling, functional genomic screening, antibody engineering, genome editing, and gene synthesis) and likely many more that remain to be discovered. Our method will greatly enable the use of synthetic DNA for these applications.

The method combines high-throughput mating of yeast clones on agar plates, a unique selectable system for combining DNA fragments, and low-cost next-generation sequencing. First, oligonucleotides are PCR-amplified from a pooled library using common primers. Second, amplicons are transformed and integrated at a specific location in the yeast genome. The transformation protocol and recipient strain are uniquely designed for ultra high-efficiency integration at the desired locus. Third, colonies (i.e., transformants) are arrayed onto agar plates and mated to a defined set of strains carrying barcodes. A collection of 1536 unique 'barcoder strains' facilitate processing of large oligo libraries. Fourth, a loxP translocation system induces site-specific recombination in the diploid, producing a selectable, contiguous stretch of DNA containing the oligo sequence adjacent to a barcode. Fifth, diploid colonies are combined, the oligo-barcode DNA amplified by PCR, and amplicons are sequenced by next-generation (e.g. Illumina) sequencing. The identity of the barcode attached to each oligo identifies the position of the strains containing the oligo DNA on the arrayed agar plate. The oligo DNA from these strains can then be extracted and used as needed.

The use of in vivo recombination to 'tag' oligonucleotide DNA to facilitate its isolation following sequencing is novel. Using this approach, the fraction of DNA containing the designed sequence is determined by the fidelity of the polymerase used to amplify it, which is several orders of magnitude better than oligonucleotide synthesis fidelity. In addition to the specific protocol described below, similar protocols could be developed based on this novel concept, for example using a host other than yeast (such as bacteria), or having the DNA oligonucleotides and DNA barcodes on plasmids rather than integrated in the genome. We are currently using Illumina's sequencing platform, but other sequencing platforms could be used. We are currently using this method to process oligonucleotides synthesized on arrays, but the method could also be useful for processing other types of DNA libraries (e.g. cDNA libraries).

General Overview

The method was performed with the following steps:
1. PCR-amplification of oligonucleotide pool (OP)
2. PCR-amplification of TranSceInt cassette (TS)
3. Transformation of OP+TS and selection on 5-fluorocytosine (5-FC) plates
4. Colony-picking into 384-well plates
5. Mating with barcoded strains
6. Selection of diploid strains that have undergone lox-recombination
7. Pooling diploid strains
8. Extraction of genomic DNA from pool
9. PCR amplification of oligonucleotide-loxP-BC cassette for sequencing
10. Library preparation
11. MiSeq-sequencing
12. Sequence data analysis
13. Cherry-picking of yeast colonies containing sequence-verified oligo DNA
14. Archiving cherry-picked strains
15. PCR-amplification of sequence-verified oligo DNA with high-fidelity polymerase Detailed Protocol:

The procedure was carried out as follows:

Step 1. PCR Amplification of Oligonucleotide Pool (OP)

PCR Reaction:
34 µl water
10 µl Q5 Reaction buffer (5×)
2 µl dNTP mix (10 mM)
1 µl forward primer (see below) (100 µM)
1 µl reverse primer (see below) (100 µM)
1 µl oligonucleotide pool
1 µl Q5 High-Fidelity DNA Polymerase PCR Program:
Step 1) 94° C. 3 minutes
Step 2) 94° C. 15 seconds
Step 3) 55° C. 15 seconds
Step 4) 68° C. 30 seconds (go back to Step 2, repeat 29 times)
Step 5) 68° C. 7 minutes Verify the PCR reactions were successful by applying gel electrophoresis to a small aliquot of each reaction (each PCR reaction is expected to yield an approximately 250 base pair (bp) product; the exact size depends on the length of the oligonucleotides amplified at the beginning). PCR products can be stored at −20° C. for 3 months.

Notes:

Specific primer pairs are used to amplify subsets of oligonucleotides from the oligonucleotide pool. In this protocol we used the 'Ras mutagenesis' subset of oligonucleotides as an example. Below is an example of a 'Ras mutagenesis' oligonucleotide. The flanking portions (3' flanking sequence, SEQ ID NO:1, 5' flanking sequence, SEQ ID NO:8), common to all sequences in this subset, are in bold. The MlyI-restriction sites (type IIS) are underlined. $[N]_{129}$ signifies the Ras-specific sequence.

GACCTGCAGT<u>GAGTCGTACG</u>[N]$_{129}$CGAGT<u>GACTCCTTCCGATCT</u>

The primers used to amplify this subset are shown below. The portion in bold anneals to the common priming sites. The underlined portion is homologous to the genomic target locus in strain #2849 (OLseq recipient strain). Note, longer homology to the genomic target may improve integration efficiency.

ras_fragment_for:
(SEQ ID NO: 2)
<u>GACTAAAGGAGGCTTTTGTCGACGGATCCGATATCGGTAC</u>**GACCT
GCAGTGAGTCGTACG** ras_fragment_rev:
(SEQ ID NO: 3)
<u>TTATACGAAGTTATGTTGCAACACACTTCCTGCTTAGGCA</u>**AGATCG
GAAGGAGTCACTCG**

Step 2. PCR Amplification of TranSceInt Cassette (TS)

PCR Reaction:
33.5 µl water
5 µl Taq Polymerase buffer (10×)
2.5 µl MgCl$_2$ (25 mM)
2.5 µl dNTP mix (10 mM)
2.5 µl DMSO
1 µl M13_for (10 µM)
1 µl M13_rev (10 µM)
1 µl plasmid pJH141 (20 ng/µl)
1 µl Taq Polymerase PCR Program:
Step 1) 94° C. 3 minutes
Step 2) 94° C. 30 seconds
Step 3) 55° C. 30 seconds
Step 4) 68° C. 1 minute (go back to Step 2, repeat 29 times)
Step 5) 68° C. 7 minutes Verify the PCR reactions were successful by applying gel electrophoresis to a small aliquot of each reaction (each PCR reaction is expected to yield a 1598 bp product). PCR products can be stored at −20° C. for 3 months.

Notes:

This PCR amplifies the TranSceInt cassette which consists of the SceI restriction enzyme under the control of the constitutive TEF1 promotor and the CYC1 terminator. Expression of SceI leads to cutting of the target locus (creating a double strand break) resulting in approximately a 50-100 fold increase in integration efficiency. The primer sequences used to amplify the cassette are shown below. The template is plasmid pJH141.

M13_for:
(SEQ ID NO: 4)
5'-GTTGTAAAACGACGGCCAGTG

M13_rev:
(SEQ ID NO: 5)
5'-TCACACAGGAAACAGCTATGACC

Step 3. Transformation of OP+TS Amplicons and Selection on 5-Fluorocytosine Plates
1. pick a single colony of the recipient strain (e.g. strain #2849) from an agar plate and inoculate into 5 ml of YPD
2. grow culture overnight to saturation
3. inoculate 1 ml of the saturated culture into 10 ml of YPD
4. grow culture for 3 to 6 hours with constant shaking at 200 rpm at 30° C.
5. transfer 1 ml of the culture into an Eppendorf tube
6. spin for 1 minute at 6000 rpm, aspirate supernatant
7. resuspend pellet in 1 ml of 100 mM LiAc
8. repeat steps 6) and 7) once
9. boil a tube with salmon sperm DNA for 15 min and then cool on ice
10. resuspend pellet in 100 µl salmon sperm DNA
11. add 20 µl of OP-PCR product and 20 µl of TS-PCR product
12. incubate for 30 minutes at 30° C.
13. resuspend the pellet in 320 µl PEG (48%)
14. add 40 µl of 1 M LiAc
15. incubate for 30 minutes at 30° C.
16. heat-shock for 45 minutes in water bath at 42° C.
17. spin for 30 seconds at 14000 rpm
18. aspirate supernatant
19. resuspend pellet in 5 ml of YPD
20. incubate overnight at 30° C.
21. vortex tube to resuspend all settled cells
22. plate aliquots of 100 µl each onto 50 5-fluorocytosine plates (see Media)
23. spread cells with glass beads
24. incubate for 3 days at 30° C. (wrap plates into plastic bag to avoid drying)

Notes:
The #2849 recipient strain contains the counter-selectable FCY1-cassette in the target locus. The FCY1-cassette is flanked by SceI-restriction sites. By co-transforming the oligonucleotide amplicon together with the TranSceInt amplicon, the integration efficiency of the oligonucleotide amplicon is greatly enhanced. Successful integration of the oligonucleotide cassette is selected by media containing 5-fluorocytosine.

Step 4. Arraying Transformants in 1536 Format
Estimate the number of colonies on all 5-fluorocytosine plates and then (accordingly) fill 384-well plates with 40 µl YPD. Briefly spin the plates to collect the media on the bottom of the well. Pick colonies with an automated colony picking robot. Seal the 384-well plates and incubate for 2 days at 30° C. (shaking is not necessary). Using a Singer ROTOR robot, pin cells from the 384-well plates onto a YPD agar plate. Combine 4 plates into one to create a 1536-well plate. Note, colony picking directly onto agar, and in 1536 format, will eliminate some of these steps and should be done if the robot is capable.

Pin the 1536 barcoder strains onto a YPD agar plate. Incubate for 1 day at 30° C.

Step 5. Mating with Barcoded Strains
Using a Singer ROTOR, pin the oligonucleotide-containing strains and the barcoded strains onto the same YPD agar plate and incubate for 1 day at 30° C.

Step 6. Barcoding of Exogenous DNA: Selection of Diploid Strains that have Undergone Lox-Recombination
Using a Singer ROTOR, replica plate the colonies onto CSM-uracil+galactose plates and incubate for 2 days at 30° C. Galactose induces expression of Cre-recombinase. Growth in the absence of uracil selects for clones that have undergone successful site-specific recombination. Note, replica plating these colonies for a second round of growth on CSM-uracil+galactose can reduce background.

Step 7. Pooling of Diploid Strains
Add 10 ml of YPD media to the surface of each of the plates and incubate for 15 minutes. Gently shake the plates to wash the colonies off the agar surface. Collect the cell suspension in a Falcon tube and vortex (the cells from each plate should be collected in separate tubes).

Step 8. Extraction of Genomic DNA from Pool
Take a small aliquot of the cell suspension (200 µl) and extract genomic DNA using the Zymo Research YeaStar Genomic DNA kit, or a similar method. Take a second aliquot of the cell suspension, spin for 1 min at 14000 rpm, aspirate the supernatant and freeze at −20° C. This sample is kept in case the first round of genomic DNA extraction fails.

Step 9. PCR Amplification of Oligonucleotide-loxP-BC Cassette for Sequencing
PCR Reaction:
30 µl water
10 µl Q5 Reaction buffer (5×)
2 µl dNTP mix (10 mM)
1 µl UP/DN primer mix (100 µM)
5 µl genomic DNA
1 µl Q5 High-Fidelity DNA Polymerase
[include a no genomic DNA control to check for primer dimers]

PCR Program:
Step 1) 94° C. 3 minutes
Step 2) 94° C. 15 seconds
Step 3) 55° C. 15 seconds
Step 4) 68° C. 30 seconds (go back to Step 2, repeated 29 times)
Step 5) 68° C. 7 minutes Verify the PCR reactions were successful by applying gel electrophoresis to a small aliquot of each reaction (each PCR reaction is expected to yield a ~425 bp product; the exact size depends on the length of the oligonucleotides amplified at the beginning). PCR products can be stored at −20° C. for 3 months.

Notes:
In this PCR common priming sites within the double-barcode region are used to amplify the oligonucleotide-loxP-BC cassette. The forward and reverse primers used for this PCR reaction contain P5 and P7, respectively, that bind to the Illumina flow cell. Each primer also contains a 6-base index (therefore each MiSeq-amplicon has two indices) that identify the sample. The use of indexed primers allow the same barcoder strain to be used multiple times in the same experiment (provided it is amplified with different index primers). In other words, each 1536 plate of diploids requires a different index pair.

Shown below is one example of such a primer pair. The portions in italics correspond to P5 and P7 in the UP- and DN-primer, respectively. The portions in bold correspond to Read1 and Read2 in the UP- and DN-primer, respectively. The underlined sequences correspond to the 6-base indices.

```
DBC-UP-1:
                                                (SEQ ID NO: 6)
AATGATACGGCGACCACCGAGATCTACACTCTTTCCCTACACGACG

CTCTTCCGATCTTGCTAAACGGATCCGATATCGGTAC

DBC-DN-5:
                                                (SEQ ID NO: 7)
CAAGCAGAAGACGGCATACGAGATCGGTCTCGGCATTCCTGCTGA

ACCGCTCTTCCGATCTATGATCTTAGATCTGATATCGGTACC
```

Step 10. Library Preparation for Illumina Sequencing

1. Purify the PCR amplicons by adding 50 µl of AMPure XP beads to 30 µL of each PCR reaction, incubate for 5 minutes at room temperature, and collect the beads using a magnetic rack.

2. Remove the supernatant and wash the beads twice with 200 µL of freshly prepared 70% ethanol while keeping the tubes in the magnetic rack.

3. Aspirate the supernatant and let the beads dry for 5 minutes.

4. Remove tubes from the magnetic rack, elute the DNA in 30 µL of de-ionized water, then reapply magnetic force to collect the beads, and transfer supernatant to a fresh tube.

5. (Optional) Analyze the size and concentration of the purified PCR amplicons using a highly sensitive electrophoretic system (such as the Bioanalyzer 2100 instrument). Samples can also be quantified with fluorescent DNA-binding dye approaches (such as the Qubit fluorometric system).

6. Dilute a small aliquot of each DNA sample 1:50,000 and 1:100,000 with KAPA Library Quantification kit dilution buffer and then quantify the concentration of every sample using the KAPA Library Quantification kit and a real-time PCR system (such as the Applied Biosystems 7900HT instrument).

Step 11. MiSeq Sequencing

1. Mix the DNA samples so that the final concentration of the resulting sequencing library is 1 nM and every sample is represented in equimolar amounts.

2. Thaw the ready-to-use reagent cartridge (containing reagents and buffer HT1) of an Illumina MiSeq Reagent kit v2 (300 cycle) for 30 minutes in de-ionized water.

3. Combine 10 µL of the sequencing library with 10 µL of 0.2 N NaOH (freshly diluted from a 2 N solution) and incubate for 5 minutes at room temperature.

4. Add 980 µL of pre-chilled HT1 buffer to the denatured sequencing library, vortex, and place on ice. The concentration of the library is now 10 pM.

5. Dilute the PhiX control stock solution to 2 nM in water, then combine 10 µL of this diluted PhiX control solution with 10 µL of 0.2 N NaOH and incubate for 5 min at room temperature.

6. Add 980 µL of pre-chilled HT1 buffer to the denatured PhiX control, vortex, and place on ice. The concentration of the PhiX control is now 20 pM and can be stored at −20° C. for 3 weeks.

7. Combine 225 µL of the denatured and diluted sequencing library (from step 12) with 12.5 µL PhiX control (from step 14) and 762.5 µL HT1 buffer. The final concentrations of the sequencing library and PhiX control are 2.25 pM and 0.25 pM, respectively.

8. Inject 600 µL of this mixture into the cartridge of the Illumina MiSeq Reagent kit and start the sequencing run on the MiSeq instrument.

Note, the number of cycles for the forward and reverse reads should be determined such that the entire length of the exogenous DNA (i.e. the oligonucleotide insert), and the 26 bp barcode, are sequenced.

Step 12. Sequence Data Analysis

1. Extract the sequencing reads from the fastq-file and use the first 6 bases in read 1 and read 2 to assign reads to samples (i.e. the different 1536A plates).

2. Use the bases in read 2 following the common primer sequence (bases 27-52) to assign reads to each barcoded strain. For the barcodes, include inexact matches within a Levenshtein distance of 1.

3. Use the bases in read 1 following the common primer sequence to identify the oligonucleotide.

4. Using the sequencing indices to separate data for each plate, create a table that lists the frequency of every oligonucleotide and its position on the plate (identified by the barcode sequence).

Step 13. Cherry-Picking of Sequence-Verified Yeast Colonies

Cherry-pick the yeast strains with sequence-verified oligonucleotides from the arrayed haploid transformants using a Singer ROTOR with 'Stinger' attachment. Note, if a copy of the diploid recombinants was made, the appropriate clones can also be cherry-picked from these. The clones can be cherry-picked into 96-well plates with liquid YPD media (100 µL per well), or higher density recipient plates (agar or liquid) if many clones are to be combined.

Step 14. Archiving Cherry-Picked Strains

Cherry-picked clones can be archived in 96 or 384 well plates in YPD+25% glycerol, and stored indefinitely at −80° C.

Step 15. PCR-Amplification of Sequence-Verified Oligonucleotide DNA

Combine equal numbers of cells from each cherry-picked clone into a tube, extract the genomic DNA as in Step 8, and PCR-amplify the oligo DNA using a high fidelity polymerase. In this PCR common priming sites flanking the oligonucleotide cassette are used for amplification. Note, the relative abundance of individual DNA molecules following the PCR is proportional to the number of cells representing each clone. Thus, it is important to combine equal numbers for cells for each cherry-picked clone.

Shown below is an example of a primer pair that can be used to amplify the sequence-verified Ras mutagenesis DNA. MlyI sites are underlined. Digestion of the PCR produce with MlyI will remove the priming sites from the DNA.

```
ras_for:
                                                (SEQ ID NO: 8)
GACCTGCAGTGAGTCGTACG ras_rev:
                                                (SEQ ID NO: 9)
AGATCGGAAGGAGTCACTCG
```

Media

YPD Plates 20 g Bacto Agar Bacto Difco 214010 (BD Microbiology)

10 g Yeast Extract Bacto Difco 212750 (BD Microbiology)

20 g Bacto Peptone Difco 211677 (BD Microbiology)

dissolve in 950 ml water and autoclave add 50 ml of 40% Dextrose Difco 215530 (BD Microbiology)

YPD Liquid Media
10 g Yeast Extract Bacto Difco 212750 (BD Microbiology)
20 g Bacto Peptone Difco 211677 (BD Microbiology) dissolved in 950 ml water
add 50 ml of 40% Dextrose Difco 215530 (BD Microbiology)
5-Fluorocytosine Plates
43.7 g DOBA 114026012 (MP Biomedicals)
dissolve in 950 ml water then add the following supplements
10 ml L-methionine (2 g/l stock) (Sigma-Aldrich M-5308)
10 ml L-histidine (2 g/l stock) (Sigma-Aldrich H-6034)
10 ml L-leucine (10 g/l stock) (Sigma-Aldrich L-8912)
10 ml L-lysine (2.5 g/l stock) (Sigma-Aldrich L-5501)
10 ml uracil (2 g/l stock) (Sigma-Aldrich U-1128)
autoclave, let cool to 50° C.
add 2 ml of 5-fluorocytosine (50 mM stock) (Sigma-Aldrich U-7129)
CSM-Uracil+Galactose Plates
20 g Bacto Agar Bacto Difco 214010 (BD Microbiology)
6.7 g Yeast Nitrogen Base without Amino Acids Difco 291940 (BD Microbiology)
0.77 g CSM-URA 114511212 (MP Biomedicals)
dissolve in 900 ml water and autoclave
add 100 ml of 20% Galactose Difco 216310 (BD Microbiology)

Example 2

Yeast Oligonucleotide Recipient and Barcoder Strains

Recipient Strains

Recipient strains are designed for high-efficiency incorporation of DNA libraries by transformation, and their subsequent tagging by mating to Barcoder strains (which are described below). All recipient strains used in this study were derivatives of strain #2797 (MATalpha, his3Δ, leu2Δ, lys2Δ, ura3Δ, ybr209w::KanMX-URA3 prom-5'URA3-Barcode-lox71-GalCre, can1::MFa1pr-HIS3-MFalpha1pr-LEU2), a derivative of SHA349 (MATalpha, his3Δ, leu2Δ, lys2Δ, ura3Δ, ybr209w::NatMX-GalCre, can1::MFa1pr-HIS3-MFalpha1pr-LEU2), that contains a partially crippled loxP site (lox71) {Albert: 1995ch, Zhang: 2002eg}, a 26 bp barcode TGCCTAAGCAGGAAGTGTGTTGCAAC (SEQ ID NO:15), the promoter and 5' end of URA3 gene followed by part of an artificial intron {Lee: 2008cl}, and the KanMX dominant drug resistant marker {Goldstein: 1999bz}. Additional details on the construction of strain #2797 can be found below (Barcoder strains). To create a recipient strain, #2797 was modified as follows. First, wild-type FCY1 was replaced with the HphMX-cassette (Hygromycin B resistance cassette); the HphMX-cassette was PCR-amplified and transformed into #2797. Transformants were selected on YPD+HygB. HygB-resistant clones were confirmed to grow on YNB+AS+Dex+leu+his+ura+5-fluorocytosine, and were confirmed to not grow on YNB+AS+leu+his+cytosine (further confirming loss of FCY1). The fcy1::HphMX deletion was also confirmed by PCR. The resulting strain was #2836. Next, the SceI-FCY1prom-FCY1-SceI cassette was inserted between the lox71 site and the 26 bp barcode of strain #2836; the 1089 bp cassette was amplified by PCR with primers that each contain one SceI site, and using the plasmid pJH143 as template, and transformed into #2836. Transformants were selected on CSM-uracil+cytosine+HygB. Successful transformants were confirmed to not grow in YPD+5-fluorocytosine (5-FC), indicating the presence of FCY1 cassette, and also by PCR using primers P45 and P40 (yielding a 1414 bp product). The resulting strain, #2849, served as the initial recipient strain, for some of the experiments described herein.

We noted that strain #2849 was prone to spontaneous loss of mitochondrial DNA which can negatively, and unpredictably, affect growth of transformants. We therefore repaired alleles at three loci known to impact mitochondrial genome stability (SAL1, CAT5, and MIP1). First, we corrected the sal1-1 allele to wild-type SAL1 using the mega 50:50 method. A correct recombinant was identified by genomic PCR and confirmed by Sanger sequencing. The resulting strain is JHY627. Next, we converted CAT5(91I) to CAT5 (91M) using primers CAT5.80.1 and CAT5.80.2 together with PCR template pJH140. A correct recombinant was identified by genomic PCR and confirmed by Sanger sequencing. The resulting strain is JHY629. Finally, we converted MIP1(661A) to MIP1(661T) using a two-step allele replacement strategy using pLND44-4 as described by Dimitrov (Genetics, 2009, pp 365-383). A correct recombinant was identified by Sanger sequencing of both the MIP1 QTL and a region 988 bp downstream that has a known plasmid error. The resulting strain is JHY650. DNA from the three QTLs was PCR amplified from the final strain, JHY650, and Sanger sequenced to confirm the desired alleles. All alleles were correct, and the pLND44-4 plasmid sequence error noted by Dimitrov was not present. In addition the barcoding/artificial-intron region of JHY650 strain was also confirmed by Sanger sequencing.

Barcoder Strains

Approximately 1536 Barcoder strains were generated for high-throughput tagging of the exogenous DNA incorporated in recipient strains. These barcoder strains are derivatives of SHA345 (MATa, his3Δ, leu2Δ, met15Δ, ura3Δ, ybr209w::GalCre-NatMX, can1::MFa1pr-HIS3-MFalphalpr-LEU2). Briefly, random barcodes were ordered as primers (IDT) and inserted into a plasmid backbone by ligation, generating a plasmid library (U3Kan66) that contains a partially crippled loxP site (lox66) {Albert: 1995ch, Zhang: 2002eg}, the barcode region, the 3' end of URA3 gene preceded by part of an artificial intron {Lee: 2008cl} and the KanMX dominant drug resistant marker {Goldstein: 1999bz}. We used the DNA from this plasmid library to replace (by yeast homologous recombination) the NatMX cassette in SHA345 with lox66-Barcode-3'URA3-URA3term-KanMX. This yields SHA345+BC strains (MATa, his3Δ, leu2Δ, met15Δ, ura3Δ, ybr209w::GalCre-lox66-Barcode-3'URA3-URA3term-KanMX, can1::MFa1pr-HIS3-MFalpha1pr-LEU2), where each strain contains a unique barcode. The genotype of each SHA345+BC strain was verified by assaying for growth on YPD+G418 (for KanMX), YPD+nourseothricin (for NatMX), and CSM+galactose-uracil following mating to a "tester strain". The barcode sequence of roughly 1100 of the SHA345+BC strains were identified by Sanger sequencing. The barcode sequence of all SHA345+BC strains were verified/identified using additional barcoder strains of the opposite mating type (see below). Mating of arrayed SHA345+BC strains to transformed recipient strains in 1536 format, followed by selection for loxP recombinants on CSM-uracil+galactose media, results in tagging (i.e. barcoding) of the exogenous DNA incorporated in recipient strains.

MATalpha barcoder strains derived from SHA349 (MATalpha, his3Δ, leu2Δ, lys2Δ, ura3Δ, ybr209w::NatMX-GalCre, can1::MFa1pr-HIS3-MFalpha1pr-LEU2) were used to verify the genotypes of MATa barcoder strains. The MATalpha barcoder strains were constructed as above. Briefly, random barcodes were ordered as primers (IDT) and inserted into a plasmid backbone by ligation, generating a second plasmid library (U5Kan71), which contains a partially crippled loxP site (lox71) {Albert: 1995ch, Zhang: 2002eg}, the barcode region, the promoter and 5' end of URA3 gene followed by part of an artificial intron {Lee: 2008cl}, and the KanMX dominant drug resistant marker {Goldstein: 1999bz}. Homologous recombination was used to replace the NatMX cassette in SHA349 with lox71-Barcode-URA3prom-5'URA3-KanMX. This produced strain #2797 (the parent for all recipient strains), as well as 768 additional SHA349+BC barcoder strains (MATalpha, his3Δ, leu2Δ, lys2Δ, ura3Δ, ybr209w::KanMX-URA3prom-5'URA3-Barcode-lox71-GalCre, can1::MFa1pr-HIS3-MFalpha1pr-LEU2). The barcode sequence in each SHA349+BC strain was verified by Sanger sequencing. We used these strains to verify/identify the barcode sequences in our SHA345+BC strains. Briefly, SHA349+BC strains were mated to SHA345+BC strains in array format, and diploids containing 'double-barcodes' were selected on CSM-uracil+ galactose media. Collective amplification of double-barcodes, followed by Illumina sequencing, was used to verify and/or identify the barcode in each SHA345+BC strain.

Example 3

Pilot Experiment #1: Gene Assembly

Our first pilot experiment was designed to demonstrate basic functioning of the system and to highlight an important application for sequence-verified oligos (i.e. synthetic gene assembly). To this end, we had synthesized 14 oligonucleotides that were each 80 bases in length. The oligos contained 20 base common priming sites with nested recognition sites for the type IIS endonuclease, MlyI. The 40 base internal nucleotide sequences unique to each oligo, overlapped each other by 20 bases, such that they could be assembled into a 300 base pair product.

Even though they were synthesized individually, oligos were combined prior to transforming our recipient strain to mimic our ultimate goal of parsing mixed oligonucleotide libraries. Following transformation, roughly 300 MATα transformants were arrayed into 384A format. These clones were then mated to barcoder strains by replica pinning. Diploid recombinants (i.e. diploids in which loxP recombination linked the barcode to the exogenous oligonucleotide DNA) were selected by replica pinning clones onto Complete Synthetic Yeast Media lacking Uracil and containing Galactose. All diploid recombinants were then collected from the plate en masse, the genomic DNA from the combined cell suspension was extracted, and the barcode-oligo locus amplified by PCR. PCR primers contained adapters for the Illumina flow cell. Paired-end sequencing reads were used to identify which barcode was attached to which oligonucleotide sequence: the forward reaction identifying the oligo, and the reverse reaction identifying the barcode.

Figure 6:
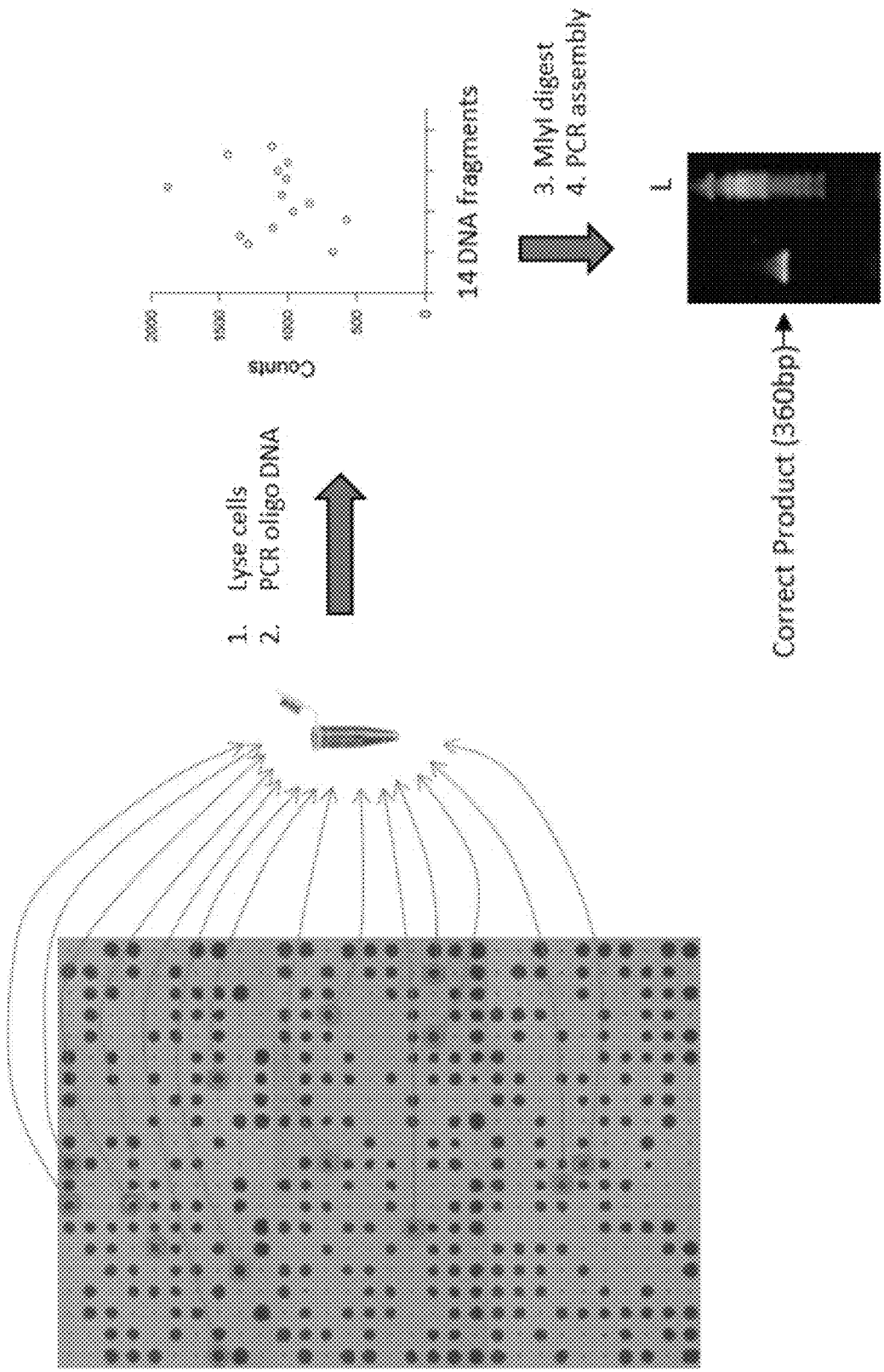
FIG. 6 shows gene assembly from 14 sequence-verified oligonucleotides. The graph shows the relative abundance (i.e., sequence counts) of 14 DNA fragments. The agarose gel shows a band for the correctly assembled 360 bp product, which includes the 300 bp assembled core, plus 60 bp introduced by the primers used for PCR.

As expected, the exogenous DNA contained in each transformant largely matched the designed/synthesized sequences. Notably, however, we identified several clones containing exogenous DNA that differed by only 1 base from the designed sequence. These presumably reflect errors that originated during oligonucleotide synthesis. Importantly, DNA synthesis errors are readily distinguished from Illumina Sequencing errors in our system, because the latter will be present in the majority of sequence reads for a given barcode. We identified at least one yeast clone for each of the 14 designed oligonucleotides. These clones were cherry-picked from a diploid array into a 96-well microtiter plate. Clones were grown to saturation, and then an equal volume of each culture was combined. The genomic DNA from this culture was then purified and the oligonucleotide DNA PCR-amplified using primers recognizing the common ends of each oligo. To verify their identity, and to determine the relative representation of each oligonucleotide fragment, we sequenced the resulting PCR product on the Illumina platform (MiSeq), and enumerated the number of reads matching each of the 14 designed oligos (FIG. 6). All 14 sequence-verified fragments were present within 4-fold relative abundance. MlyI digestion was used to remove the common priming sequences from the pooled fragment, and PCR was used to generate the fully assembled product, which was verified by agarose gel electrophoresis. The 360 bp product includes the 300 bp assembled core, plus 60 bp introduced by the primers used for PCR.

These results demonstrate the ability to parse out perfect DNA sequences from a complex mixture, and also the ability to combine those sequences in near equal abundance to facilitate gene assembly. We expect the efficiency of multi-fragment assembly will be enhanced as individual fragments approach equimolar concentrations. Our results indicate that other assembly strategies (e.g. Gibson Assembly, or Yeast Assembly) will also benefit from using the building blocks generated by our approach. Array-based DNA synthesis platforms can efficiently synthesize oligonucleotides up to ~200 bases in length. Extracting subsets of oligos for a given assembly typically requires the inclusion of common priming sites that are unique to each subset. Moreover, extracting a small number of fragments from libraries containing thousands of other sequences may require sequential PCR amplification steps using multiple nested priming sites and primers. This can add significant cost to large scale DNA synthesis efforts. Our approach can extract different subsets using a single set of common primers, thereby simplifying this process and allowing more of the synthesized oligo's sequence to be used in the actual assembly (and not simply as a priming site).

Example 4

Pilot Experiment #2: Molecular Probes

We next aimed to establish the scalability of the method. We, and others, have previously developed and optimized genotyping technology based on hybridization of oligonucleotide probes to specific DNA sequences. These "molecular probes" are 5'-phosphorylated oligonucleotides that are 105 bases in length, of which 60 bases are homologous to the target sequence. Thousands of unique molecular probes can be used in a single reaction, and therefore, oligonucleotides produced from array-based synthesis represent a cost-effective approach for producing molecular probes. Nevertheless, there are several drawbacks that limit the utility of array-synthesized oligonucleotides for this application. First, the concentrations of the individual probes vary greatly and cannot be easily determined. Second, DNA synthesis errors affect a significant fraction of the oligonucleotide pool: in a pool of 105-mers, for example, a typical synthesis error rate of 1 in 150 bases will result in ~50% of the oligonucleotides having an incorrect sequence.

Finally, access to an individual probe in the library is not possible unless common priming sites are incorporated into its design a priori.

We applied our methodology to improve the performance of a molecular probe library designed to detect, identify, and quantitate bacteria, principally in water and sewage. Briefly, a MATα haploid "recipient" strain was transformed with an oligonucleotide library (purchased from CustomArray) representing the 7051 probes directed against 353 bacteria (~20 probes per bacteria). Roughly 35,000 transformants were robotically arrayed on agar plates and mated to MATα "barcoder" strains, each of which contains a unique 26 bp barcode. Cre-lox recombination was then used to physically link the barcode to the oligonucleotide DNA in the diploid yeast. Illumina sequencing of the barcoded oligos revealed the location of 3322 yeast clones containing a sequence-perfect molecular probe of interest. These clones were cherry-picked from the arrayed haploid collection and the molecular probe DNA isolated by PCR using a high-fidelity DNA polymerase.

Figure 8A:
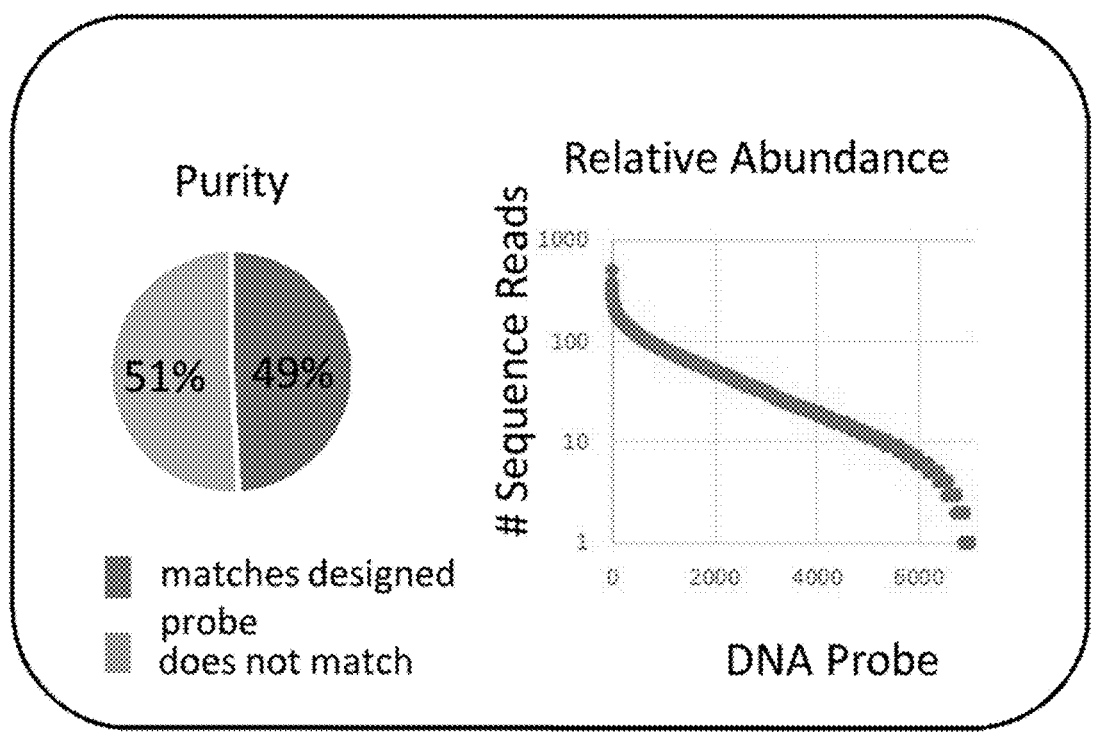
FIGS. 8A and 8B show a paired-end Illumina sequencing analysis of probe libraries generated by CustomArray.
Figure 8B:
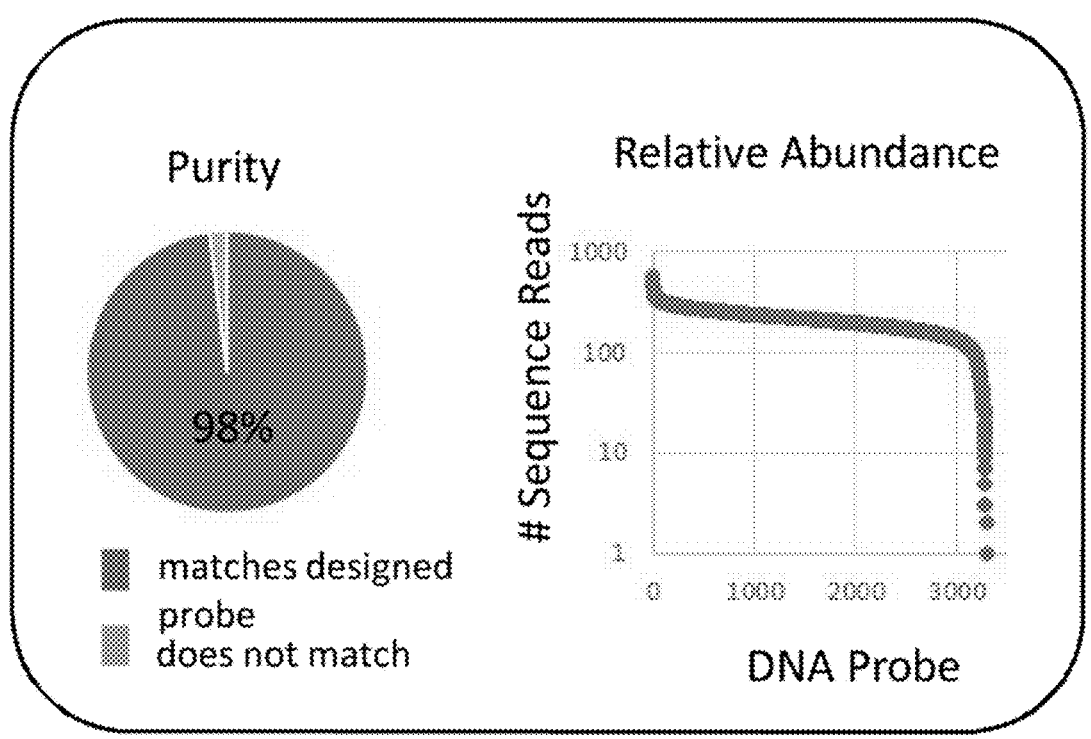

We employed paired-end Illumina sequencing to compare the composition of our molecular probe library before and after the above processing. Using primers containing the requisite sequencing adapters, we amplified the molecular probe library directly from the CustomArray library, or from the 3322 clones isolated above, and subjected both PCR products to next-generation sequencing. We then enumerated the sequencing reads matching perfectly to the designed molecular probes, restricting our analysis to cases where the forward and reverse sequencing reads were identical so as to mitigate the confounding effects of sequencing-derived errors. Consistent with the advertised error frequency, only ~49 percent of sequencing reads from the CustomArray library matched a designed sequence (FIG. 8A; left). In addition, while the majority of designed probes were detected by sequencing, the relative abundance of individual probes varied greatly in this library (FIG. 8B; right). On the other hand, DNA produced by our method was highly pure, with ~98% of sequencing reads matching a designed probe (FIG. 8B; left). Moreover, the vast majority of sequence-verified molecular probes, were present in near equimolar concentrations (FIG. 8B; right). In addition to these benefits, probes produced using our method that can be accessed individually and indefinitely from frozen yeast stocks.

Notably, the analysis above revealed a small number of probes that were poorly represented in our molecular probe library even after processing in yeast (FIG. 8B; see far right of right plot). Closer examination revealed that these probes were either derived from colonies that spontaneously acquired growth defects (due to mitochondrial genome instability; a common problem in the parental strain), or were derived from 'mixed' colonies containing two or more clones that were inadvertently picked and processed. The former issue was addressed by introducing genetic changes in our recipient strain to promote mitochondrial stability (see strains section). The latter issue could be addressed in future experiments by improving the analysis of the oligo-barcode sequencing data (i.e. by identifying cases where multiple oligo sequences were linked to the same barcode).

It is also notable that isolating oligonucleotides that are poorly represented in the original library (i.e. the oligo pool produced by array-based synthesis) will generally require screening many more transformants than those which are abundant. Because of the redundancy in our experimental design above, isolating half (n=3322) of the original library (n=7051) was sufficient. However, some applications may require all DNA fragments to be recovered. As processing more and more colonies ultimately yields "diminishing returns", re-ordering missing fragments, or employing strategies for selective amplification of rare sequences, will likely be more cost-effective.

Finally, molecular probes are typically single-stranded oligonucleotides, whereas the DNA produced from yeast are double-stranded PCR products. To convert our double-stranded library to single-stranded DNA, we employed a previously described strategy to remove the common priming sites and undesired stand. Briefly, the double-stranded PCR product is first digested in BsaI (leaving a 5' overhang on one end), then dephosphorylated with alkaline phosphatase, and then digested with MlyI (leaving a blunt end on the other end). Lambda exonuclease is then used to selectively degrade the undesired strand. Thus, the double-stranded DNA produced by our method can be readily converted to single-stranded DNA if needed.

Although preferred embodiments of the subject invention have been described in some detail, it is understood that obvious variations can be made without departing from the spirit and the scope of the invention as defined herein.

What is claimed is:

1. A method for sequence verification of an oligonucleotide from a composition comprising a mixture of oligonucleotides, the method comprising:
   a) providing the composition comprising the mixture of oligonucleotides, wherein each oligonucleotide comprises common priming sites for amplification;
   b) amplifying one or more oligonucleotides;
   c) transforming a plurality of host cells with the amplified oligonucleotides, wherein each host cell comprises a target locus, wherein each amplified oligonucleotide is integrated at a site within the target locus of a host cell, said target locus comprising a first recombination target site for a site-specific recombinase, wherein the first recombination site is adjacent to the site where the oligonucleotide is integrated at the target locus;
   d) plating the plurality of transformed host cells in a first ordered array on media suitable for growth of the host cells;
   e) culturing the plurality of transformed host cells under conditions whereby each host cell produces a colony of clones in the first ordered array, wherein each colony of clones has a position in the first ordered array and comprises a different oligonucleotide integrated at the target locus, and further wherein the position of each oligonucleotide in the first ordered array is not known;

f) providing a plurality of barcoder cells in a second ordered array, wherein each position of the first ordered array corresponds to a position in the second ordered array, and further wherein each barcoder cell comprises a nucleic acid comprising a second recombination target site for the site-specific recombinase adjacent to a barcode sequence that identifies a position of the barcoder cell in the second ordered array;

g) introducing the oligonucleotide integrated at the target locus of a clone from each position in the first ordered array into a barcoder cell from each corresponding position in the second ordered array, thereby forming a plurality of oligonucleotide-barcoder cells;

h) introducing the site-specific recombinase into each oligonucleotide-barcoder cell, wherein the site-specific recombinase catalyzes site-specific recombination between the first recombination target site and the second recombination target site, thereby translocating the oligonucleotide to a position adjacent to the barcode sequence to generate a nucleic acid comprising a barcode-oligonucleotide fusion sequence in each oligonucleotide-barcoder cell;

i) combining the barcode-oligonucleotide fusion sequences from each of the plurality of oligonucleotide-barcoder cells; and j) sequencing the combined barcode-oligonucleotide fusion sequences to identify and verify each oligonucleotide sequence, wherein the barcode in each barcode-oligonucleotide fusion sequence identifies the position in the first ordered array of a colony comprising the adjacent sequence-verified oligonucleotide.

2. The method of claim 1, wherein the target locus is within the genome of each host cell, and the oligonucleotides are amplified with a primer comprising an integration targeting sequence that is sufficiently homologous to a genomic target locus of the host cell, such that amplicons of the oligonucleotides integrate into the genome at the target locus in the transformed host cell by homologous recombination.

3. The method of claim 2, further comprising using a selectable marker that selects for clones that have undergone successful integration of an oligonucleotide at the genomic target locus.

4. The method of claim 1, wherein the target locus is within the genome of each host cell, the method further comprising transforming the plurality of host cells with a recombinant polynucleotide encoding a restriction enzyme operably linked to a promotor, wherein the restriction enzyme is expressed in the plurality of host cells and creates a double strand break at the genomic target locus that facilitates integration of an oligonucleotide at the genomic target locus.

5. The method of claim 1, wherein the oligonucleotides are amplified with a primer comprising a targeting sequence that is sufficiently homologous to the target locus on a plasmid in the host cell, such that the oligonucleotide amplicons integrate at the target locus into the plasmid in the transformed host cell.

6. The method of claim 5, further comprising using a selectable marker that selects for clones that have undergone successful integration of an oligonucleotide at the plasmid target locus.

7. The method of claim 5, further comprising transforming the plurality of host cells with a recombinant polynucleotide encoding a restriction enzyme operably linked to a promotor, wherein the restriction enzyme is expressed in the plurality of host cells and creates a double strand break at the target locus of the plasmid that facilitates integration of the oligonucleotide at the target locus into the plasmid.

8. The method of claim 1, wherein the oligonucleotides are amplified with a primer comprising a recombination target site capable of undergoing recombination with the recombination target site of the barcoder cell.

9. The method of claim 1, wherein the sequence of each oligonucleotide is flanked by a common 5' restriction site and a common 3' restriction site.

10. The method of claim 9, further comprising performing a restriction digest that selectively cleaves each oligonucleotide at the common 5' restriction site and the common 3' restriction site to produce a restriction fragment.

11. The method of claim 10, further comprising cloning the restriction fragment into a vector.

12. The method of claim 11, wherein the vector is a plasmid or viral vector.

13. The method of claim 12, wherein the vector further comprises the first recombination target site.

14. The method of claim 1, wherein transforming the plurality of host cells comprises introducing vectors comprising the oligonucleotides into the host cells.

15. The method of claim 1, wherein the host cells are prokaryotic cells or eukaryotic cells.

16. The method of claim 15, wherein the host cells are yeast.

17. The method of claim 15, wherein the host cells are bacteria.

18. The method of claim 1, wherein the site-specific recombinase system is a Cre-loxP site-specific recombinase system, a Flp-FRT site-specific recombinase system, a PhiC31-att site-specific recombinase system, or a Dre-rox site-specific recombinase system.

19. The method of claim 1, further comprising using a selectable marker that selects for clones that have undergone successful site-specific recombination.

20. The method of claim 1, wherein amplifying the oligonucleotides is performed using a method selected from the group consisting of polymerase chain reaction (PCR), nucleic acid sequence-based amplification (NASBA), transcription mediated amplification (TMA), strand displacement amplification (SDA), and ligase chain reaction (LCR).

21. The method of claim 20, wherein the oligonucleotides are amplified using PCR.

22. The method of claim 1, wherein said plating the plurality of transformed host cells in the first ordered array is performed with an automated robotic device.

23. The method of claim 1, further comprising amplifying the sequence-verified oligonucleotide.

24. The method of claim 1, further comprising removing contaminating oligonucleotides that have incorrect sequences.

25. The method of claim 23, wherein a set of universal primers capable of hybridizing to the common priming sites are used to amplify all the sequence-verified oligonucleotides in parallel.

26. The method of claim 23, wherein a set of selective primers are used to selectively amplify a subset of the sequence-verified oligonucleotides.

27. The method of claim 1, wherein the mixture of oligonucleotides comprises a probe library or a primer library.

28. The method of claim 27, further comprising using the sequence-verified oligonucleotide as a primer or a probe.

29. The method of claim 1, further comprising creating a library of sequence-verified oligonucleotides by collecting clones comprising sequence-verified oligonucleotides.

30. The method of claim 29, wherein the library of sequence-verified oligonucleotides is a probe library or a primer library.

31. A method for sequence verification of one or more oligonucleotides from a composition comprising a mixture of oligonucleotides, the method comprising:
  a) providing the composition comprising the mixture of oligonucleotides, wherein each oligonucleotide comprises common priming sites for amplification;
  b) amplifying one or more oligonucleotides;
  c) transforming a plurality of haploid recipient yeast host cells with the amplified oligonucleotides, wherein each host cell comprises a target locus, wherein each amplified oligonucleotide is integrated at a site within the target locus of a host cell, said target locus comprising a first recombination target site for a site-specific recombinase, wherein the first recombination site is adjacent to the site where the oligonucleotide is integrated at the target locus;
  d) plating the plurality of transformed recipient yeast host cells in a first ordered array on media suitable for growth of the recipient yeast host cells;
  e) culturing the plurality of transformed recipient yeast host cells under conditions whereby each recipient yeast host cell produces a colony of clones in the first ordered array, wherein each colony of clones has a position in the first ordered array and comprises a different oligonucleotide integrated at the target locus, and further wherein the position of each oligonucleotide in the first ordered array is not known;
  f) providing a plurality of haploid barcoder yeast cells in a second ordered array, wherein each barcoder yeast cell is capable of mating with the recipient yeast host cells and comprises a nucleic acid comprising a second recombination target site for the site-specific recombinase adjacent to a barcode sequence that identifies the position of the barcoder yeast cell in the second ordered array, and wherein each position of the first ordered array corresponds to a position in the second ordered array;
  g) mating each haploid recipient yeast host cell from the first array with the haploid barcoder yeast cell in the corresponding position on the second ordered array to produce diploid yeast cells;
  h) introducing the site-specific recombinase into each diploid yeast cell, wherein the site-specific recombinase catalyzes site-specific recombination between the first recombination target site and the second recombination target site, thereby translocating the oligonucleotide to a position adjacent to the barcode sequence in each diploid yeast cell to generate a nucleic acid comprising a barcode-oligonucleotide fusion sequence in each diploid yeast cell;
  i) combining the diploid yeast cells comprising barcode-oligonucleotide fusion sequences;
  j) isolating nucleic acids from the combined diploid cells;
  k) sequencing the combined barcode-oligonucleotide fusion sequences to identify and verify each oligonucleotide sequence, wherein the barcode in each barcode-oligonucleotide fusion sequence identifies the position in the first ordered array of a colony comprising the adjacent sequence-verified oligonucleotide; and
  l) picking one or more clones comprising the sequence-verified oligonucleotides from the colonies in the first ordered array identified by their barcodes.

32. The method of claim 31, wherein the recipient yeast host cells are of strain MATα and the barcoder yeast cells are of strain MATa.

33. The method of claim 31, wherein the recipient yeast host cells are of strain MATa and the barcoder yeast cells are of strain MATα.

34. A method for sequence verification of a cDNA from a composition comprising a mixture of cDNAs, the method comprising:
  a) providing the composition comprising the mixture of cDNAs, wherein each cDNA comprises common priming sites for amplification;
  b) amplifying one or more cDNAs;
  c) transforming a plurality of host cells with the amplified cDNAs, wherein each host cell comprises a target locus, wherein each amplified cDNA is integrated at a site within the target locus of a host cell, said target locus comprising a first recombination target site for a site-specific recombinase, wherein the first recombination site is adjacent to the site where the cDNA is integrated at the target locus;
  d) plating the plurality of transformed host cells in a first ordered array on media suitable for growth of the host cells;
  e) culturing the plurality of transformed host cells under conditions whereby each host cell produces a colony of clones in the first ordered array, wherein each colony of clones has a position in the first ordered array and comprises a different cDNA integrated at the target locus, and further wherein the position of each cDNA in the first ordered array is not known;
  f) providing a plurality of barcoder cells in a second ordered array, wherein each position of the first ordered array corresponds to a position in the second ordered array, and further wherein each barcoder cell comprises a nucleic acid comprising a second recombination target site for the site-specific recombinase adjacent to a barcode sequence that identifies a position of the barcoder cell in the second ordered array;
  g) introducing the cDNA integrated at the target locus of a clone from each position in the first ordered array into a barcoder cell from each corresponding position in the second ordered array, thereby forming a plurality of cDNA-barcoder cells;
  h) introducing the site-specific recombinase into each cDNA-barcoder cell, wherein the site-specific recombinase catalyzes site-specific recombination between the first recombination target site and the second recombination target site, thereby translocating the cDNA to a position adjacent to the barcode sequence to generate a nucleic acid comprising a barcode-cDNA fusion sequence in each cDNA-barcoder cell;
  i) combining the barcode-oligonucleotide fusion sequences from each of the plurality of cDNA-barcoder cells;
  j) sequencing the combined barcode-cDNA fusion sequences to identify and verify each cDNA sequence, wherein the barcode in each barcode-cDNA fusion sequence identifies the position in the first ordered array of a colony comprising the adjacent sequence-verified cDNA.

35. The method of claim 1, further comprising picking a clone comprising the sequence-verified oligonucleotide from the colony in the first ordered array identified by the barcode, and isolating the sequence-verified oligonucleotide from the clone comprising the sequence-verified oligonucleotide.

36. The method of claim 31, further comprising picking a clone comprising the sequence-verified oligonucleotide from the colony in the first ordered array identified by the barcode, and isolating one or more sequence-verified oligonucleotides from the clones comprising the sequence-verified oligonucleotides.

37. The method of claim 34, further comprising picking a clone comprising the sequence-verified cDNA from the colony in the first ordered array identified by the barcode, and isolating the sequence-verified cDNA from the clone comprising the sequence-verified cDNA.

38. The method of claim 1, wherein combining the barcode-oligonucleotide fusion sequences from each of the plurality of oligonucleotide-barcoder cells comprises combining the plurality of oligonucleotide-barcoder cells prior to isolating the barcode-oligonucleotide fusion sequences from the oligonucleotide-barcoder cells.

39. The method of claim 34, wherein combining the barcode-cDNA fusion sequences from each of the plurality of cDNA-barcoder cells comprises combining the plurality of cDNA-barcoder cells prior to isolating the barcode-cDNA fusion sequences from the cDNA-barcoder cells.

40. The method of claim 35, wherein said picking a clone is performed with an automated robotic device.

41. A method for in vitro gene synthesis, the method comprising:
   a) isolating a set of sequence-verified oligonucleotides according to the method of claim 35, wherein said oligonucleotides collectively comprise the sequence of the gene; and
   b) performing gene assembly with the set of sequence-verified oligonucleotides.

42. The method of claim 41, wherein gene assembly is performed using ligase chain reaction (LCR) or assembly PCR.

* * * * *